United States Patent [19]
dos Santos

[11] Patent Number: 6,009,747
[45] Date of Patent: Jan. 4, 2000

[54] METHOD FOR EVALUATING DRILLING FLUIDS

[75] Inventor: Hélio Maurício Ribeiro dos Santos, Rio de Janeiro, Brazil

[73] Assignee: Petroleo Brasileiro S.A.-Petrobras, Rio de Janiero, Brazil

[21] Appl. No.: 09/084,427

[22] Filed: May 27, 1998

[51] Int. Cl.$^7$ .......................... E21B 49/02; G01N 23/22; G01N 31/36

[52] U.S. Cl. .................. 73/53.01; 73/152.07; 73/54.42; 73/61.46

[58] Field of Search .............................. 73/53.01, 54.42, 73/61.46, 61.72, 61.74, 61.76, 152.07, 152.09; 252/8.51, 49.3; 507/240, 129, 139, 110; 175/50

[56] References Cited

U.S. PATENT DOCUMENTS

| | | | |
|---|---|---|---|
| 3,503,250 | 3/1970 | Cotton et al. ............................... | 73/61 |
| 3,833,340 | 9/1974 | Jones et al. ......................... | 23/230 HC |
| 3,900,449 | 8/1975 | Rembold et al. .................. | 260/78 UA |
| 4,198,207 | 4/1980 | Ladov et al. ....................... | 23/230 HC |
| 4,221,125 | 9/1980 | Oliver et al. ......................... | 73/61.1 R |
| 4,251,809 | 2/1981 | Cheney ..................................... | 340/603 |
| 4,257,775 | 3/1981 | Ladov et al. ....................... | 23/230 HC |
| 4,439,491 | 3/1984 | Wilson ..................................... | 428/408 |
| 4,589,277 | 5/1986 | Collins et al. ........................ | 73/61.1 R |
| 4,608,859 | 9/1986 | Rockley ..................................... | 73/153 |
| 4,790,180 | 12/1988 | Sinnokrot ................................. | 73/153 |
| 4,852,400 | 8/1989 | Wingrave ................................. | 73/153 |
| 4,920,792 | 5/1990 | DiFoggio ................................. | 73/153 |
| 4,963,273 | 10/1990 | Perricone et al. .................... | 252/8.51 |
| 5,182,942 | 2/1993 | Hartel et al. .......................... | 73/61.46 |
| 5,205,164 | 4/1993 | Steiger et al. ........................... | 73/153 |
| 5,279,971 | 1/1994 | Schneider ................................. | 436/139 |
| 5,415,024 | 5/1995 | Proffitt et al. .......................... | 73/61.44 |
| 5,433,105 | 7/1995 | Takahashi et al. ..................... | 73/61.46 |
| 5,452,601 | 9/1995 | Hori et al. .............................. | 73/54.42 |
| 5,518,933 | 5/1996 | Ishibashi ................................. | 436/163 |
| 5,519,214 | 5/1996 | Houwen et al. ........................ | 250/256 |
| 5,527,627 | 6/1996 | Lautzenhiser et al. ................. | 428/615 |
| 5,546,798 | 8/1996 | Collee et al. ........................ | 73/152.09 |
| 5,635,458 | 6/1997 | Lee et al. ................................ | 507/240 |

OTHER PUBLICATIONS

SPE 38644 "Concepts and Misconceptions of Mud Selection Criteria: How to Minimize Borehole Stability Problems?" H. Santos, SPE, Petrobras and S. S. B. da Fontoura, SPE, Catholic University of Rio de Janeiro (PUC–Rio) pp. 781–796.

Cms workshop lectures vol. 3 "Thermal Analysis in Clay Science" J. W. Stucki and D. L. Bish Technical Editors and F. A. Mumpton Managing Editor. Oct. 1990.

*Primary Examiner*—Hezron Williams
*Assistant Examiner*—J. David Wiggins
*Attorney, Agent, or Firm*—Sughrue, Mion, Zinn, Macpeak & Seas, PLLC

[57] ABSTRACT

A method for evaluating drilling fluids to be used with clay-rich rocks such as shales which comprises collecting shales so as to preserve the downhole hydration condition and then submitting such preserved shale to Thermo-Gravimetric Analysis, so as to obtain the derivative curve of mass with respect to temperature, then immersing a sample of the same piece of rock in the drilling fluid of which the interaction with the clay-rich rock is to be ascertained and obtaining TGA analysis at successive periods of time of immersion of the sample, so as to determine the modifications undergone by the sample immersed in the drillling fluid. From the modifications undergone by the sample it is possible to evaluate the adequacy of the drilling fluid to be contacted with the clay-rich rock.

11 Claims, 15 Drawing Sheets

METHOD FOR EVALUATING DRILLING FLUIDS

FIELD OF THE INVENTION

The present invention relates to a method for evaluating drilling fluids and specially to improvements in the selection of the present drilling fluids to be contacted with clay-rich rocks such as shales.

The method of the present invention comprises the use of the Thermo-Gravimetric Analysis (TGA) as a tool for determining the qualitative mineralogical composition of a clay-rich rock in its native, downhole hydration state as well as the modifications in its mineralogy and hydration state when immersed in a test fluid for different periods of time.

Further, whenever the chemical reaction undergone by a constituent mineral is known, the method of the present invention is an adequate tool for the quantitative determination of that particular mineral in a sample.

Besides determining the type of water (free, bound or crystalline) present in a clay-rich rock, the present method is also a tool for the quantitative determination of the amount of each type of water in a clay-rich rock.

BACKGROUND INFORMATION

Problems related to well stability are considered the main single source of resource losses during drilling. If the cost of the drilling fluid itself is added, amounts can be substantial.

During oil and gas drilling operations, long sections of argillaceous formations having clay minerals as major constituents, such as shales, mudstones, siltsones, and claystones, often have to be penetrated before reaching the hydrocarbon bearing zones. Various drilling problems, such as bit balling, swelling or sloughing of wellbore, stuck pipe, and dispersion of drilled cuttings, are frequently encountered while drilling such formations. This is especially true when using water-based drilling fluids and can result in tremendous losses of operation time and increases in operation costs. Due to their tendency to become unstable upon contact with water, such argillaceous formations are also commonly referred to as water-sensitive shales.

Upon contact of a water-based mud with shales, water adsorption occurs immediately. This causes clays to hydrate and swell resulting in stress and/or volume increases. Stress increases can induce brittle or tensile failure of the formations, leading to sloughing, cave in and stuck pipe. Volume increases, on the other hand, reduce the mechanical strength of shales and cause swelling of wellbore, disintegration of cuttings in drilling fluid, and balling up of drilling tools. In order to prevent water adsorption and clay hydration from occurring, it is believed that oil-based drilling fluids are the most effective for this purpose.

The inhibitive action of oil-based drilling fluids is based on the emulsification of brine in oil, which acts as a semi-permeable barrier that materially separates the water molecules from being in direct contact with the water-sensitive shales. However, there are many restrictions to the use of oil-based drilling fluids in view of their detrimental effect on the environment.

On the other hand, it is well-known that the correct choice of the fluid to be used during the drilling of an oil well is directly responsible for the economical and technical success of the operation. In many instances, the interaction between the fluid and the rock being drilled causes undesirable effects with costs which are increased beyond all expected levels.

Several hypotheses and theories were advanced to try to explain the mechanisms which govern the instability of an oil well, one of the most widely known being the physico-chemical changes caused by the contact of shales with the drilling fluid. In order to minimize the drawbacks caused by these changes, various additives have been developed, which are compounded to the base fluid according to the nature of the rock to be drilled.

The contact of shales with aqueous drilling fluids may cause swelling of shales, this being attributable to at least two mechanisms, crystalline and osmotic. Crystalline swelling or surface hydration results from the adsorption of mono-molecular layers of water onto the shale surfaces. Osmotic swelling occurs if the cation concentration on the surfaces of the shale is greater than that in the surrounding fluid. Ion hydration and water adsorption causes an increase in the hydrodynamic volume. For swelling to occur, the shale must interact with the water taking and/or sharing hydroxyl groups of the water with it. Normally shale inhibition is achieved by adding divalent cations or potassium ions through base exchange or by adding encapsulating and bridging polymers to the water based fluids or by the use of oil based fluids.

In the available drilling fluid systems, the evaluation and classification of the adequacy of the drilling fluid to the rock to be drilled (or being drilled) is of paramount importance for the success of the drilling operation in the well.

The presently available methods for the qualitative and quantitative evaluation of the adequacy and quality of the drilling fluid relate mainly to changes and alterations in the weight of the rock under test in response to the action of a drilling fluid.

Thus, the Slake Durability Test compares the weight of a dried sample before and after immersion in the test fluid. The weight of the dried sample is the weight after drying in an oven for 24 hours. It is evaluated that the lesser the weight loss from the sample, the more adequate is the fluid, since less dispersion was caused in the solution.

The Hot Rolling Test consists of a similar procedure, however the sample is rolled in the fluid at a temperature which is higher than ambient.

The Linear Swelling Test is based on the assumption that some clay minerals such as montmorillonites are able to absorb huge amounts of water when exposed to an aqueous fluid, this causing the swelling of the shale. Thus, this test measures, for a cylindrical sample of rock, the expansion in the axial direction as a function of the immersion time of the sample in the test solution. The expansion or contraction of the sample is measured as a percentage relative to the original length of the test sample. In spite of the fact that doubts persist on the interpretation of the obtained results, it is believed that the best drilling fluid is that one which causes the least expansion of the rock sample. Generally various fluid compositions are tested, in order to find that one which will cause the slightest possible expansion and preferably a certain degree of contraction in the sample.

Tests for the measurement of the swelling of a clay-rich shale such as a shale when contacted with an aqueous solution have been suggested by the International Society of Rock Mechanics (ISRM). The Swelling Pressure Test may be found for example in the patents by Ronald Steiger, see U.S. Pat. No. 5,275,063. Referring to the controversial aspect of the swelling of clay minerals, the fluid which will cause the least swelling pressure on the shale would be the most appropriate, since it would cause the minor possible changes in the shale. In some of the tests the swelling pressure is calculated from the measurement of the sample deformation.

In qualitative tests, a visual and tactile inspection of the sample is effected after immersion of the rock in the test fluid.

The X-Ray Diffraction (XRD) method is used as a tool for evaluating the mineralogy of a sample which has been previously dried and powdered.

The patent literature is abundant in references on the subject of the present application.

U.S. Pat. No. 4,963,273 teaches a modified liquid phase drilling fluid having desirable properties of shale swelling inhibition, lubrication, and high temperature performance. Shale inhibition is the ability of a process to retard the hydration of shales whereby they remain intact and basically in their original size, shape and volume. The fluid comprises a liquid phase containing a water phase and a water-soluble component selected from polyhydric alcohols, glycol, glycol ethers, etc., ethylene oxide-propylene oxide copolymers (EO-PO); a viscosifier; and a filtration control agent. It is alleged that the circulation of the drilling fluid into, through and out of said subterranean well will cause that the drilling fluid contacts formation particulate matter in the bore of the well. The water-soluble component is considered as providing lubricity and shale inhibiting properties comparable to those of an oil-based drilling fluid without the adverse effects thereof.

U.S. Pat. No. 5,205,164 teaches a method for determining drilling fluid density for stabilizing a wellbore including obtaining shale cuttings from a wellbore. Shale cuttings are obtained from a wellbore and their index properties, including but not limited to surface area, is measured; mean effective stress around the wellbore is calculated using the geostatic overburden in situ stress, the field pore pressure, and the total stress around the wellbore; the in situ shale strength is determined using a correlation between surface area, mean effective stress and shale strength; and drilling fluid density is determined using the shale strength. It is assumed that shale strength correlations can be used at a rig site to predict stable wellbore conditions. Shale cuttings are not preserved from dehydration.

U.S. Pat. No. 5,645,458 teaches a water-based drilling fluid that comprises a water-miscible glycol, with a molecular weight of less than about 200, at a concentration of from 30 to 70% by weight of the aqueous phase of the drilling fluid; an organic cationic material or organic salt of potassium such as choline hydroxide, choline chloride, choline carbonate in a range from 3% by weight up to saturation, based on the aqueous phase of the drilling fluid; a filtration control agent for lowering fluid loss of the drilling fluid; a viscosifier for suspension of solids and weighting material in the drilling fluid; and water. It is alleged that the inhibitive effects of the described fluids on water-sensitive shales have been evaluated by conducting swelling tests, dispersion tests and triaxial tests conducted under simulated downhole conditions. The aim of the suggested composition is to replace the water with a polar fluid which can compete with water for adsorption but will not severely weaken the mechanical strength of argillaceous rocks when adsorbed.

On examining the information sources on the subject it is clear that on the one hand simple tests such as the Slake Durability Test and the Hot Rolling Test are available for determining the interaction of fluids and clay-rich rocks while on the other hand XRD is a sophisticated tool which is able to depict the mineralogy of a sample which has been dried and powdered, so that its hydration state in the downhole condition and after contact with a test fluid cannot be established.

It is then clear that none of these tests, either by themselves or combined in any way, are able to assess the rock-fluid interaction on a truly preserved, downhole condition rock sample.

Thus, in spite of all the progress achieved in this field, the open literature invariably discloses processes focusing on shales which have been tested in a dehydrated condition, this leading to altered results which in turn affect the proposed improvements in drilling fluid compositions. This, as expected, leads to losses due to inadequate drilling fluid compositions. These observations are in line with the contents of the co-pending application "A Method for the Evaluation of Shale Reactivity", also in the name of Mr. Hélio M. R. dos Santos, inventor of the present application.

On the other hand, the characterization of a shaly rock, that is, the determination of the presence or not of swelling-inducing minerals, would certainly be helpful in devising the most adequate drilling fluid for a specific rock composition.

Thermo-Gravimetric Analysis or TGA is a well-known technique based on the principle that mass losses from a certain sample at a defined temperature correspond to the presence of specific substances present in the sample under test.

On a TGA experiment, each mineral has its own signature, that is, it is possible to at least qualitatively identify substances in a sample, for example a shale. Thus by associating the shale signature and that from the individual minerals, it is possible to determine the composition of a shaly rock.

Santos, H. and da Fontoura, S. A. B., in SPE paper n° 38644 presented at the 1997 SPE Annual Technical Conference and Exhibition, San Antonio, Tex., Oct. 5–8, 1997 "Concepts and Misconceptions of Mud Selection Criteria: How to Minimize Borehole Stability Problems?" discuss the mechanisms of swelling and selection of drilling fluids. It is stated that shale swelling is strongly related to both the amount and distribution of water within the rock. Water present in a shale may be free, interlayer, bound or crystalline water. From their experimental observations on shaly rocks authors concluded that efforts should focus not on the fact that shale swells, but rather, if the downhole shale swells. This is because it could be seen that shale only swells if it loses some of its original water, disturbing its equilibrium. On the contrary, in downhole condition, the shale is in physical and chemical equilibrium, the reaction being minimal when in contact with water, this being shown by experiments with truly preserved shales, that is, shales which have not dehydrated and therefore preserve the original, downhole hydration condition. Therefore both smectite content and period of air-exposure time will influence the swelling of a shale sample. Authors recommend careful handling procedure in the laboratory in order to preserve the downhole hydration condition of the shales.

It seems clear from the state-of-the-art technique that measurements on the rock-fluid interaction are effected on non-preserved shales, with the ensuing erroneous results. On the contrary, and according to a patentably distinguishing feature of the present invention, the rock-fluid interaction as measured by the modification of the TGA graph is effected on a sample free of contact with the drilling fluid or mud while are kept the original, downhole hydration conditions of the rock. The present method thus makes possible to effect measurements which reproduced the downhole conditions of the tested rock sample.

Therefore, the technique is in need of a method for exactly determining the rock composition and its water content under downhole condition, and thus evaluating in an accurate and precise way the changes undergone by a shaly sample when in contact with any drilling fluid. Such a method, which employs TGA for determining the rock composition is described and claimed in the present application.

SUMMARY OF THE INVENTION

Broadly speaking, the present invention is directed to a method for evaluating and selecting drilling fluids through the characterization of the shaly rock to be contacted with such fluids, with the aid of Thermal Gravimetric Analysis (TGA).

The present method makes possible to determine: i) the mineralogical composition of the clay-rich rock or sample in its preserved, native state or downhole condition, this leading to the knowledge of the several kinds of water in the rock; ii) the variation in mineralogy and content of each kind of water of the sample after immersion in test fluids.

The method for evaluating drilling fluids comprises the following steps:
  collecting downhole samples of the clay-rich rock to be analyzed keeping it free from dehydration so as to preserve the downhole hydration condition and obtain preserved samples;
  determining the mineral composition, type and amount of water by submitting the preserved sample to a TGA analysis;
  immersing a sample of the same piece of clay-rich rock in the test fluid whose effect is to be evaluated;
  analyzing the sample immersed in the test fluid with the aid of TGA at regular time intervals;
  comparing mineralogy and kind and amount of water of the as-collected, preserved sample as obtained by TGA analysis with the same parameters of the sample which has been contacted with the test fluid, also obtained by TGA;
  evaluating the adequacy of the tested drilling fluid from the modification observed in the shale sample.

Therefore, the present invention provides a method for evaluating drilling fluids to be used in clay-rich rocks with the aid of Thermo Gravimetric Analysis, the method permitting to assess the mineralogy and kinds of water of the sample in its native state as well as any modifications of these parameters when the sample is immersed in a test fluid for determined periods of time relative to the native state of the sample.

The present invention provides further a method for conveniently detect changes in the distribution of free, interlayer, bound and crystalline water in a clay-rich rock, so that interaction with different drilling fluids or muds may be monitored and the effect of additives on the rock structure may be evaluated.

Based on entirely new concepts concerning preservation of water content of shale samples and interaction of these samples with fluids, the present invention provides further a method for evaluating the shale-fluid interaction which ultimately leads to suggestions to effectively minimize borehole stability problems.

BRIEF DESCRIPTION OF THE DRAWINGS

FIG. 1A attached is a TGA graph for the clay mineral smectite SAz-1 (calcium montmorillonite) while

PREFERRED MODE—DETAILED DESCRIPTION

Figure 1A:
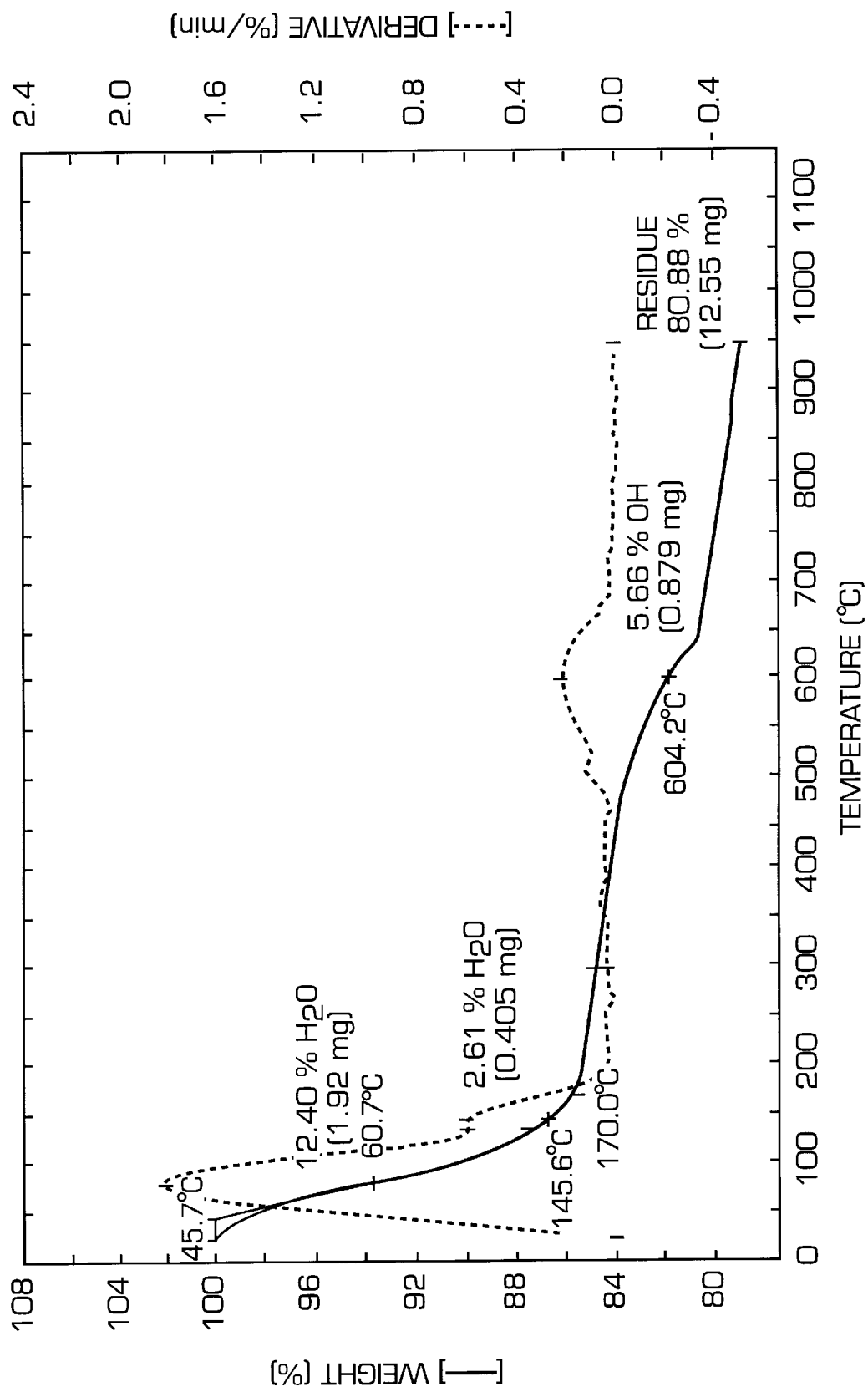

The method for evaluating drilling fluids according to the present invention is based on the concept that any measurement effected on a shale must be done on a preserved shale sample, that is, a shale sample whose hydration conditions are as close as possible from those of downhole shales.

Therefore the expression preserved shale as used in the present specification and claims means that experiments and measurements are effected on a shale which has been collected and preserved in mineral oil at all times, before the measurement is effected, so as not to disturb the water content inside the shale sample.

The preserved shale sample to be submitted to analysis by TGA may be a core or cuttings, that is, pieces of rock cut by the drill bit during drilling. The advantage of using cuttings is their availability. However, the size of cuttings should be at least 0.5 cm so that results are not influenced by the layer which has been exposed to the drilling fluid. The larger the cuttings the better it is.

As said before, samples, either cuttings or cores, should be preserved by immersion in mineral oil so as to avoid dehydration by exposure to air. Cuttings should be recovered from the shale shaker immediately after being separated from the drilling fluid, avoiding exposure to air. The excess drilling fluid should be withdrawn from the sample with the aid of a piece of paper before immersion of the cuttings in a protective fluid such as mineral oil. The use of water as cleaning fluid should be expressly avoided. If cores are used as shaly samples, immediately after retrieving the rock from the core barrel, the core is cleaned in order to eliminate excess of mud cake and drilling fluid and immersed in mineral oil.

After being collected from the well, shale samples should be kept immersed, in an oil-bearing sealed reservoir, the sample being completely immersed in mineral oil. Samples which are going to undergo analytical tests are equally preserved in smaller, easier to handle flasks, for example beakers.

As the TGA instrument operates with rather small samples, weighing of from 10 to 80 mg, the actual sample to be tested is simple to obtain: the required amount may be collected by rubbing the surface of either cuttings or core.

The TGA instrument operates by placing the sample within the instrument which comprises a highly accurate weighing device. Heating is applied and the mass of sample is constantly monitored.

Usually the test result is presented as a graph of weight of sample vs. time or weight of sample vs. temperature. The lower curve of the graph is the curve derivative of weight change. The amount of free water present in the sample may be obtained directly from the graph of the weight change observed between ambient temperature and 110° C. The adsorbed water may be obtained between 110° C. and 250° C. However there is still some controversy regarding these temperature limits in view of the release of water which is adsorbed in the smectite layers, such water being released at temperatures lower than 110° C.

The derivative curve provides the characterization of the sample. Each constituent of the rock shows a typical reaction at a certain temperature, which is identified from peaks in the derivative curve.

As the TGA instrument works by heating the sample, this heating should be effected at a constant rate, since the shape of the peaks may vary as a function of the heating rate. Although heating rates may vary within a certain range, in the present application results were obtained by applying a heating rate of 10° C./min.

The method for characterizing clay-rich or shaly samples from a borehole with the aid of TGA comprises first determining the TGA graphs or curves for pure samples of the minerals present in a shale, such as smectite, calcite and kaolinite. TGA graphs of well-known minerals are available from usual literature sources.

Once the typical shape or peak of a mineral as characterized by TGA is known, it will be possible to recognize it in a shaly sample containing that mineral and TGA tested. Further, the alterations and changes suffered by a typical peak when the same shaly sample has been submitted to interaction with a test fluid may be detected by a TGA test.

On testing shaly samples, in spite of some modifications in the shape of each peak or even slight differences in the temperature where the peak corresponding to a certain mineral normally appears, it is possible to obtain, for a shaly sample, a signature which is typical of that particular sample.

When a core is used as a source of the sample to be tested in the TGA instrument, it is advised to cut a piece of 3 to 5 cm height, of any shape. On cutting with a saw, the sample to be tested in the TGA instrument should be collected from inside the test piece since the outer layer cut by the saw shows different properties than the original, native rock. Further, any layer which has been in contact with the drilling fluid should also be wiped off.

When cuttings are used as a source of mass for the TGA instrument, it is important that the outer layer which was in contact with the drilling fluid be removed. Therefore, very small cuttings are inadequate for this test since the mass left after the contaminated layer has been removed is too small.

As set forth above, according to the present method, TGA graphs should be obtained on a shaly sample duly preserved and free of any contact with whatever fluid. Then, in order to ascertain the influence or the interaction of a drilling fluid with that same shaly sample, TGA graphs should be obtained as a function of immersion time.

In order to characterize the rock as a function of the time the shaly rock is contacted with the test fluid, the same piece of rock already TGA tested is then immersed in the test fluid and samples are retrieved from this same piece of shaly rock to effect TGA tests every 12 hours or at least every 24 hours.

Once the TGA graphs of both the original sample preserved as close as possible in downhole conditions and the same sample submitted to the interaction with a drilling fluid have been obtained, the comparison between the graphs allows to draw interesting conclusions.

Thus, for each sample, original and after interaction with fluid, the figures for free, adsorbed and crystalline water can be known, as well as the presence of a few minerals in the shaly rock. The swelling of the rock or its dehydration may be monitored by comparing the figures for free water, that is, weight loss up to 110° C.

Further, it is possible to determine the smectite content of shaly samples from TGA curves. Smectite being the mineral constituent which confers the clayish character to a rock, and it being the only clay mineral which has interlayer water (release of interlayer water begins around 65° C.), the derivative curve shows the presence of this mineral in a sample. For minerals with low smectite content an inflection is shown in the TGA curve (see FIG. 9) while for those rocks with high smectite content a separate peak may be indicated (see FIG. 8).

The structural modification undergone by the shale may be followed with the aid of the derivative curve for high temperature values. Above 400° C. a modification in the structural water of the clay minerals may be observed. Even the modification of other minerals may be observed, for example the amount of calcite. Particularly regarding calcite, its amount is influenced by the kind of salt solubilized in the test fluid, that is, KCl, $CaCl_2$ or NaCl. The higher or lower dissolution of calcite will be a function of the composition of the test fluid, mainly of the amount of calcium present in the solution.

The usefulness of the Thermo-Gravimetric Analysis as an effective tool for detecting even slight changes in water content and type in shaly samples will now be demonstrated by the following considerations and corresponding FIGURES.

FIGS. 1 to 4 are TGA graphs of minerals which may be found in shales (from Bish, D. L. and Duffy, C. J. (1990) Thermogravimetric Analysis of Minerals in *CMS Workshop lectures, Vol 3, Thermal Analysis in Clay Science*, J. W. Stucki, D. L. Bish, and F. A. Mumpton, eds. The Clay Minerals Society, Boulder, Colo., 0000-000).

FIG. 1A illustrates a TGA graph for smectite SAz-1, that is, calcium montmorillonite. The graph shows two-stage low-temperature dehydration and dehydroxylation.

Figure 1B:
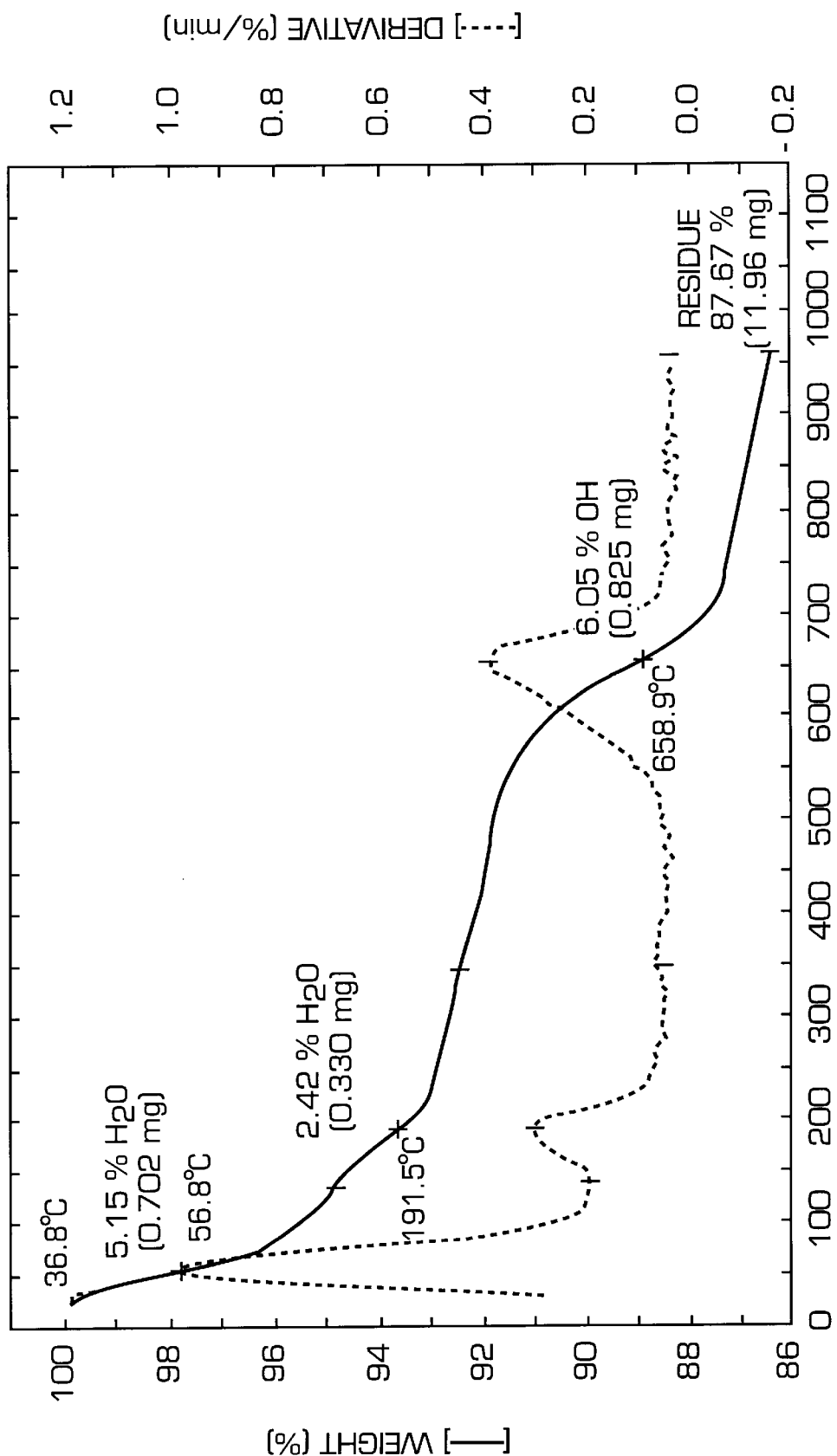
FIG. 1B is a TGA graph for sodium montmorillonite.

FIG. 1B is the TGA graph for smectite SWy-1(Na-montmorillonite) showing two-stage low-temperature dehydration and dehydroxylation.

Figure 2:
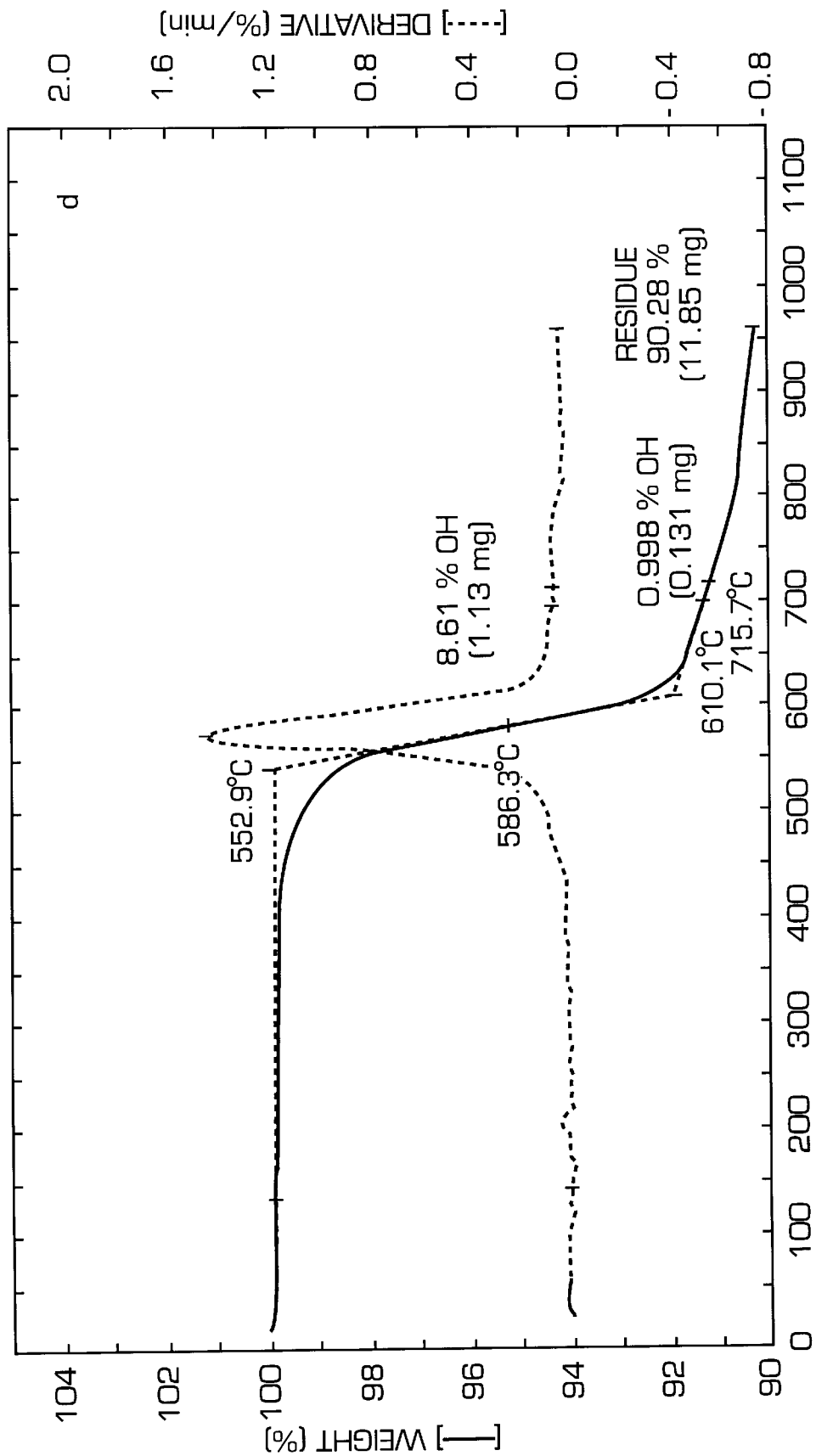
FIG. 2 attached is a TGA graph for the clay mineral chlorite.

FIG. 2 is the TGA curve for the clay-mineral ripidolite chlorite, CCa-1.

Figure 3:
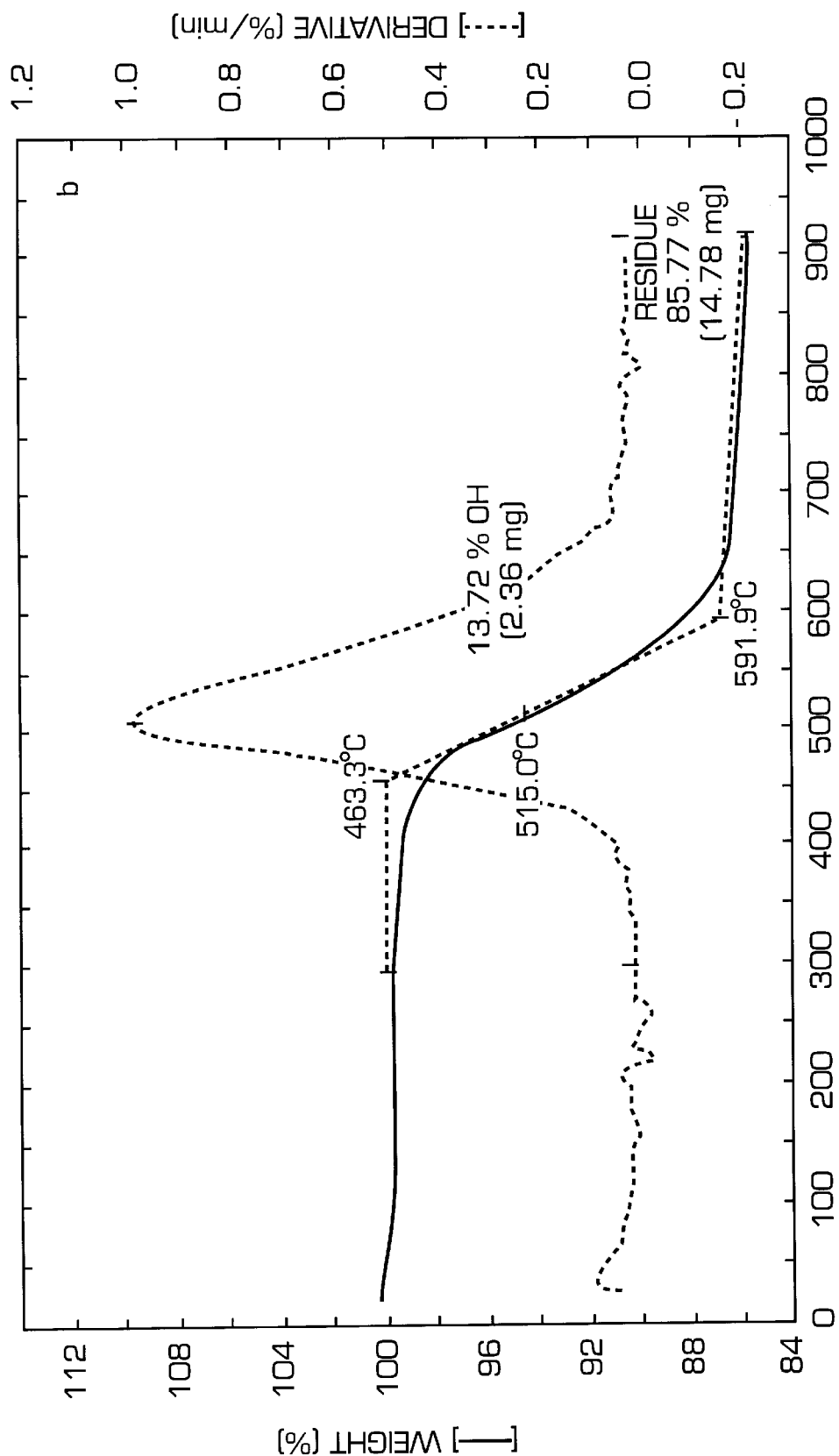
FIG. 3 attached is a TGA graph for the clay-mineral kaolinite.

FIG. 3 is a TGA graph for kaolinite Kga-1, showing mass loss due to loss of crystalline water around 550° C.; only water from OH on the structure of the mineral is released. There is no free water up to 110° C.

Figure 4:
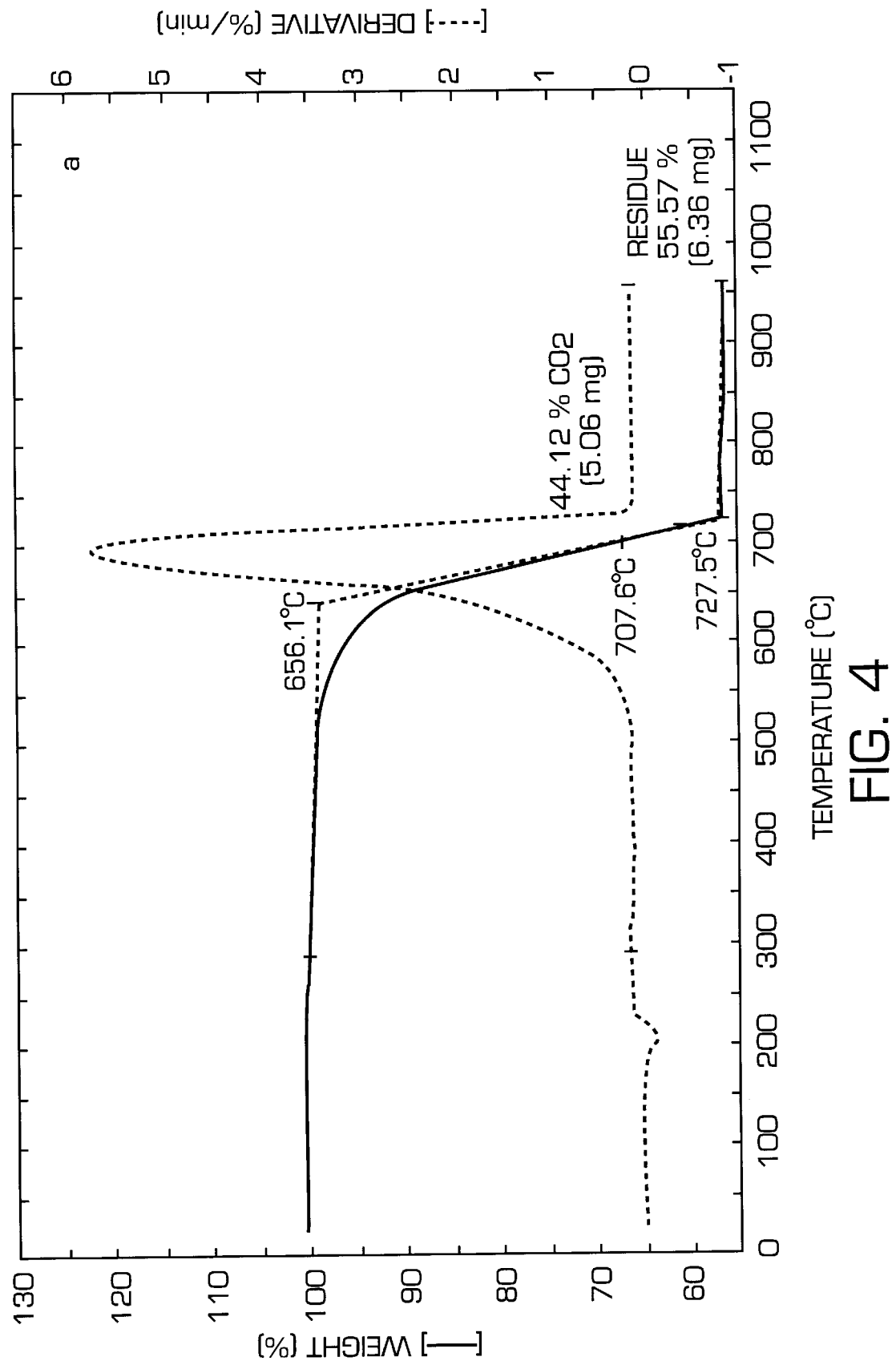
FIG. 4 attached is a TGA graph for calcite.

FIG. 4 illustrates a TGA graph for calcite indicating mass loss due to $CO_2$ released around 700° C., as indicated by a peak on the derivative curve. The amount of calcite may be estimated from the mass of $CO_2$ lost, when the peak is clearly isolated. Since one mole of calcite yields one mole of $CO_2$, a quantitative determination of the amount of calcite in a sample may be inferred from the TGA graph. Therefore TGA is an adequate tool for the quantitative determination of a mineral provided its peak in the graph is well-characterized and the reaction undergone by the mineral is well-known.

FIGS. 5 to 10 are TGA graphs of shales.

Figure 5:
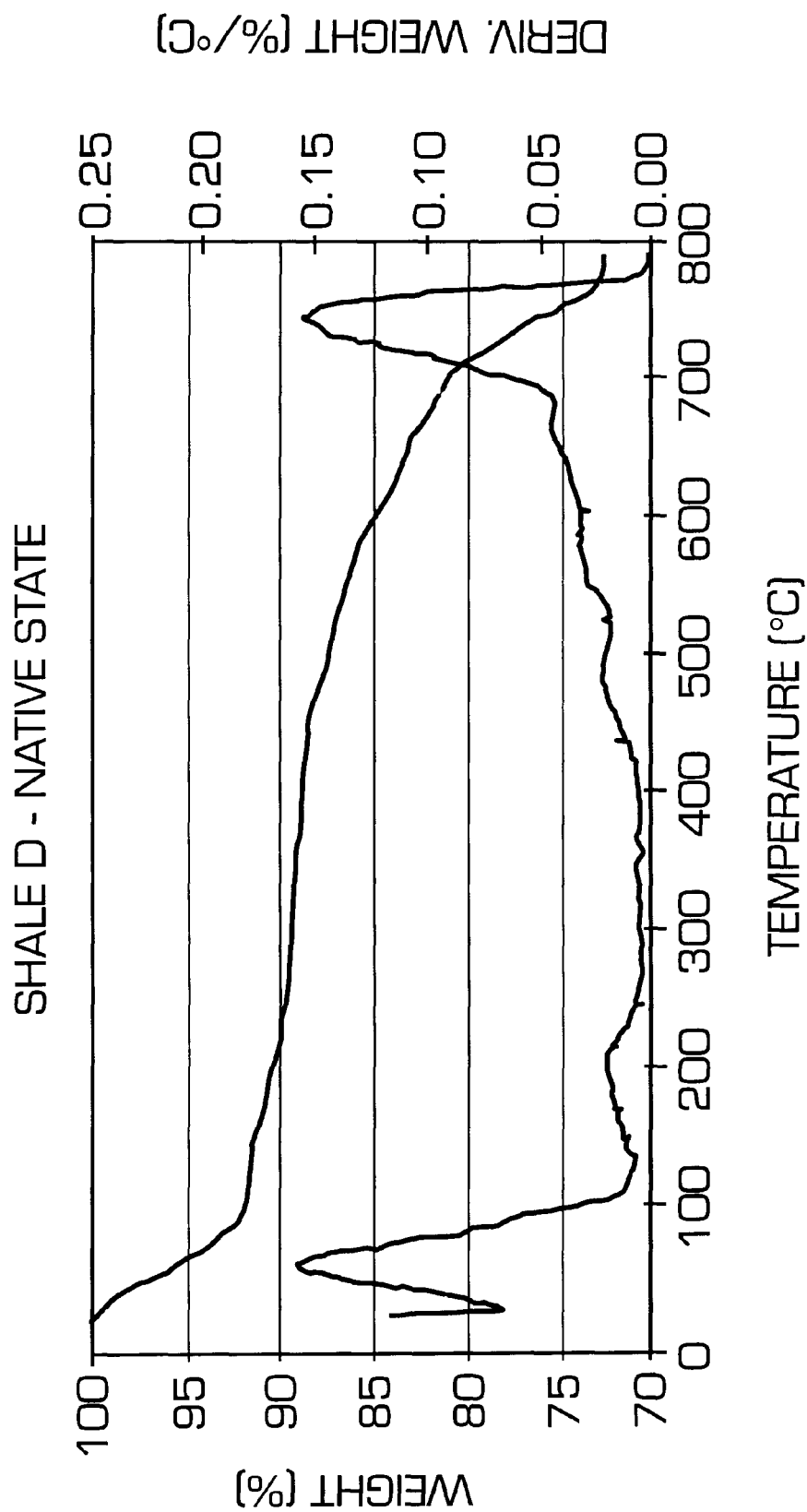
FIG. 5 attached is a TGA graph for a sample of Shale B.

FIG. 5 is a TGA graph of a sample of Shale B. The inflexion in the derivative curve around 80° C. indicates the presence of interlayer water in smectite.

Figure 6:
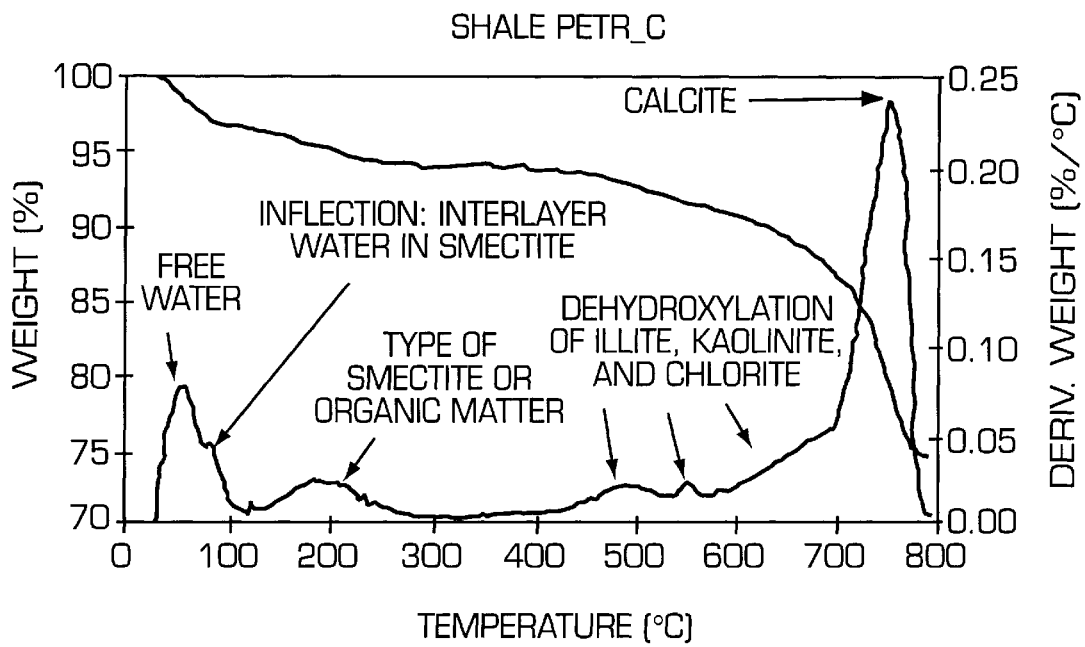
FIG. 6 attached is a TGA graph for a sample of Shale C.

FIG. 6 is a TGA graph of a sample of Shale Petr-C where free water and inflection due to interlayer water may be observed. This Figure shows that the presence of smectite in a sample may be detected by observing the derivative curve up to 100° C. Since interlayer water requires more energy to be released than free water, there will be a different weight loss rate for each of these water types. As smectite is the only clay mineral which has interlayer water, and the peak for the onset of release of this water is around 65° C., an inflection (for low smectite content) or a separate peak (for high smectite content) on the derivative curve indicates the presence of this mineral. Note that the inflection is very pronounced in shale Petr-C. Two distinct peaks of dehydroxylation may be seen, probably indicating illite and kaolinite. The ascending curve between 600° C. and 700° C. might indicate the presence of feldspar. The calcite peak is very well defined.

Figure 7:
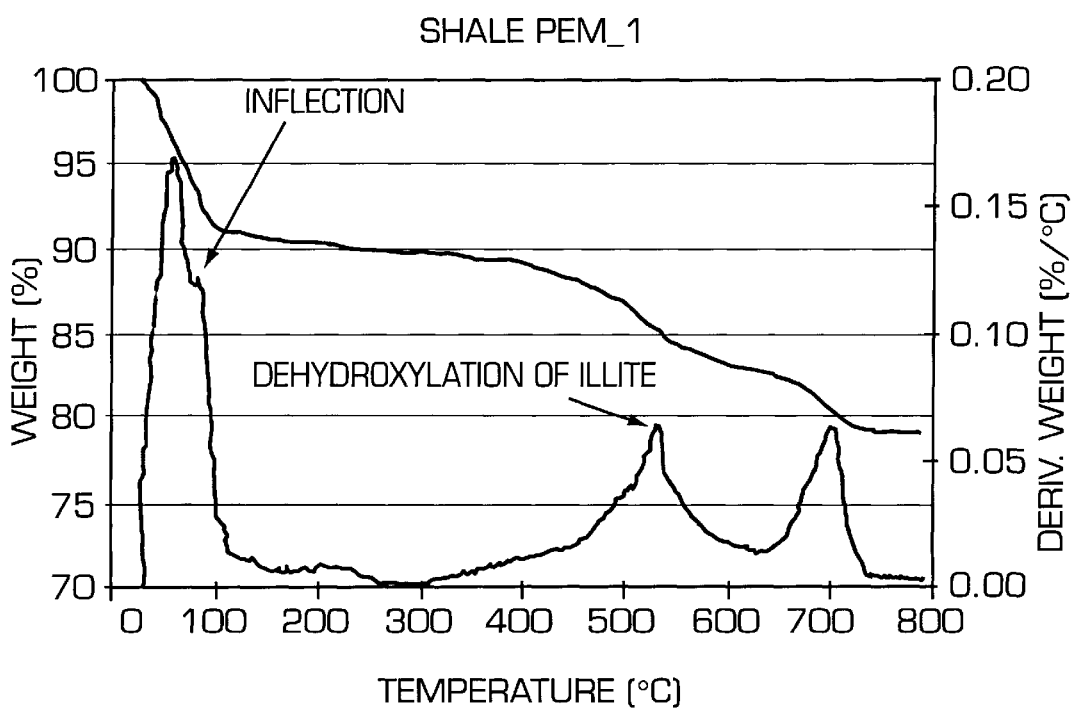
FIG. 7 attached is a TGA graph for a sample of Shale Pem-1.

FIG. 7 is a TGA graph of shale Pem-2, of low smectite content, which is indicated by the quasi-complete absence of inflection on the derivative curve below 100° C.

Figure 8:
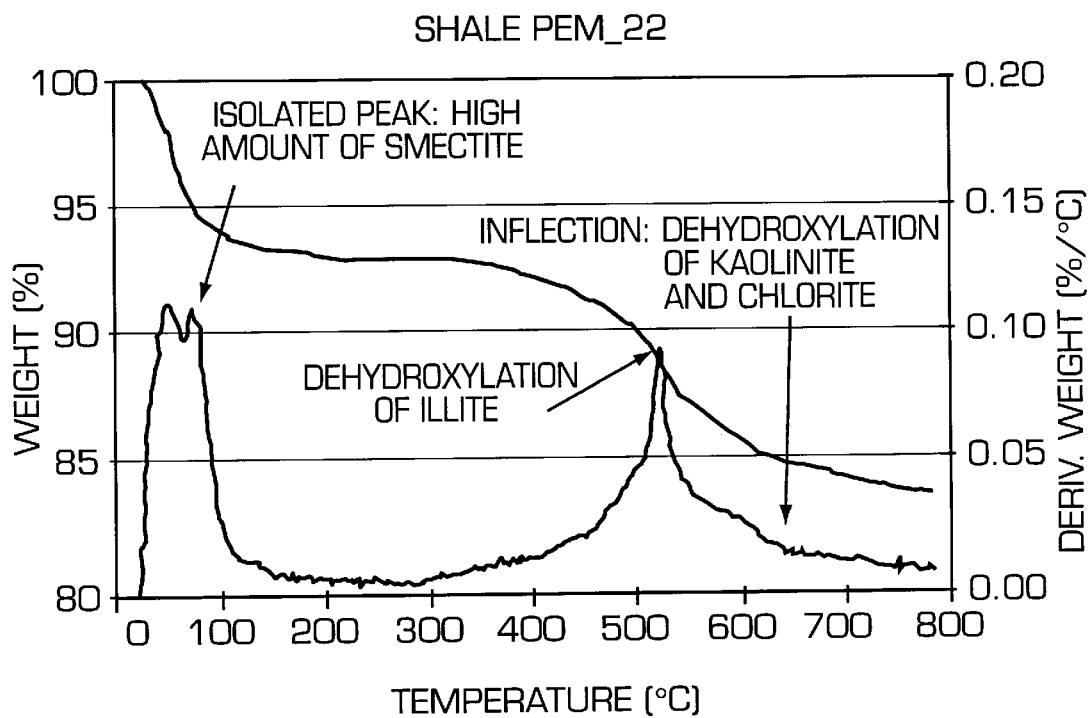
FIG. 8 attached is a TGA graph for a sample of Shale Pem-22.

FIG. 8 is a TGA graph of shale Pem-22, of high smectite content. This may be ascertained by the presence of a separate peak for smectite just below 100° C. It can be seen that from the shape and temperature level of the peaks for dehydroxylation the difference in clay minerals present in the shales can be identified. For example, Pem-22 shale has no calcite.

Figure 9:
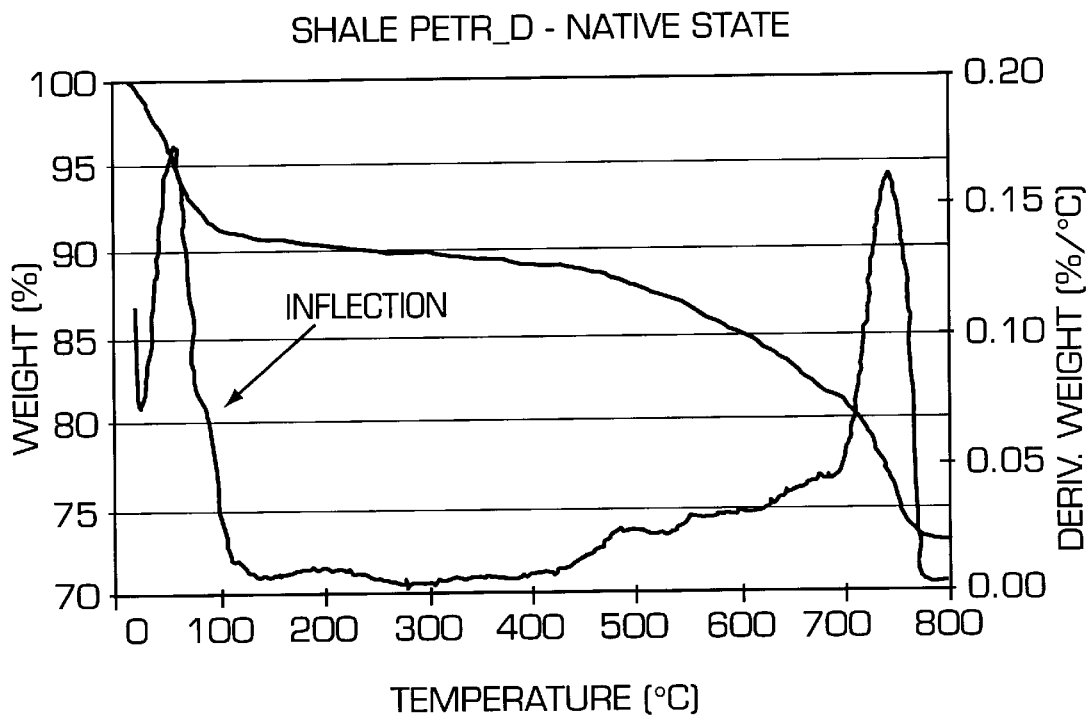
FIG. 9 attached is a TGA graph for a sample of Shale Petr-D in the downhole, native state.
Figure 10:
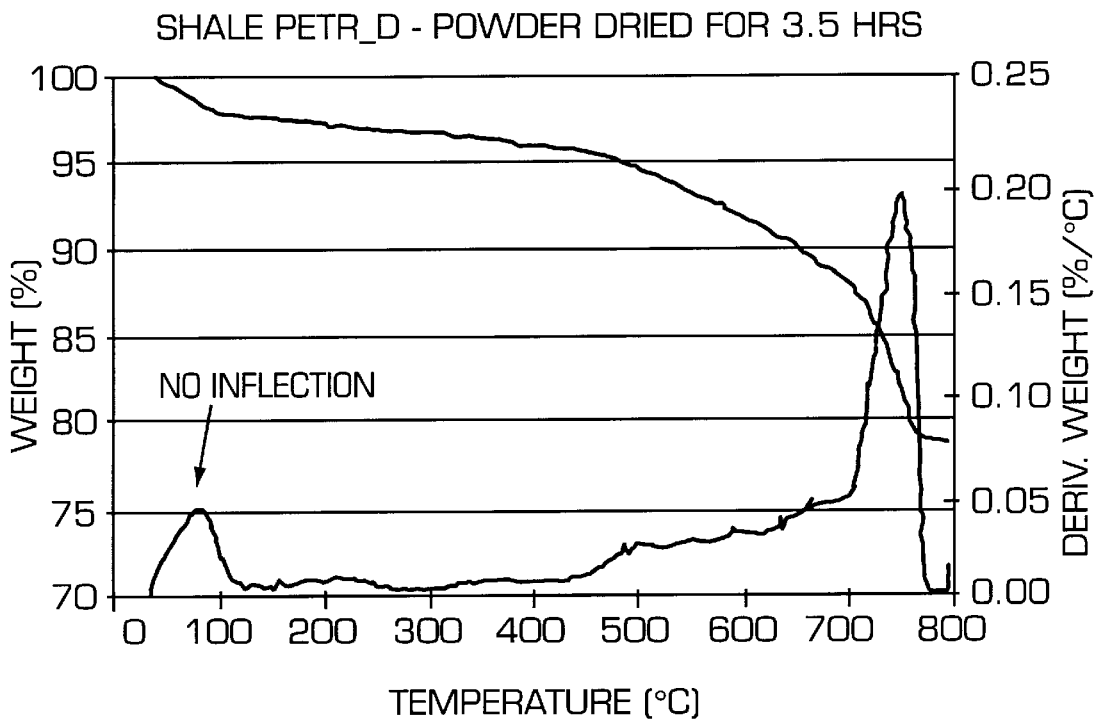
FIG. 10 attached is a TGA graph for a sample of Shale Petr-D after 3.5 hour dehydration period.

FIG. 9 is a TGA graph for a sample of Shale Petr-D in the native state. When preparing the sample for analysis, twice the amount required was scratched from the rock: half was analyzed in the native state and half was left exposed to air for 3.5 hours. The inflection shows the presence of a not very large amount of smectite. FIG. 10 shows the TGA graph of the 3.5 hour air-dried sample. It is apparent that all the free water has been removed just by air exposure. The only water left is a relatively low amount of interlayer water (no inflection), as expected from the low amount of smectite.

Reproducibility of TGA Tests

Figure 11:
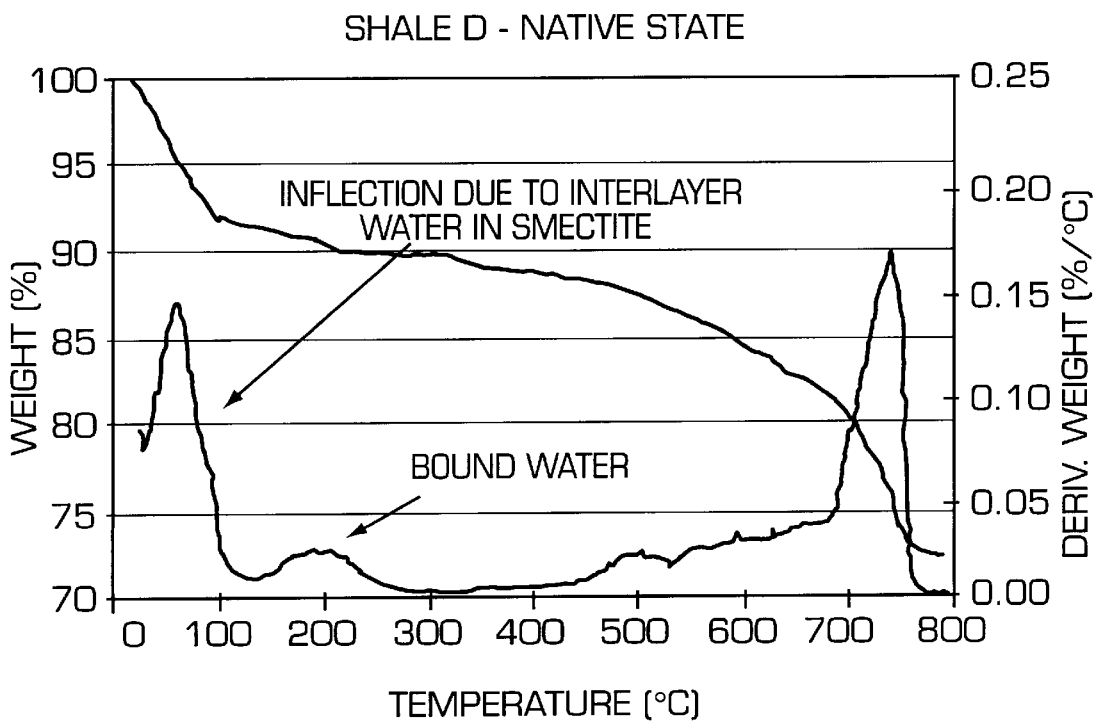
FIG. 11 attached is a TGA graph for a sample of Shale D in the native state.
Figure 12:
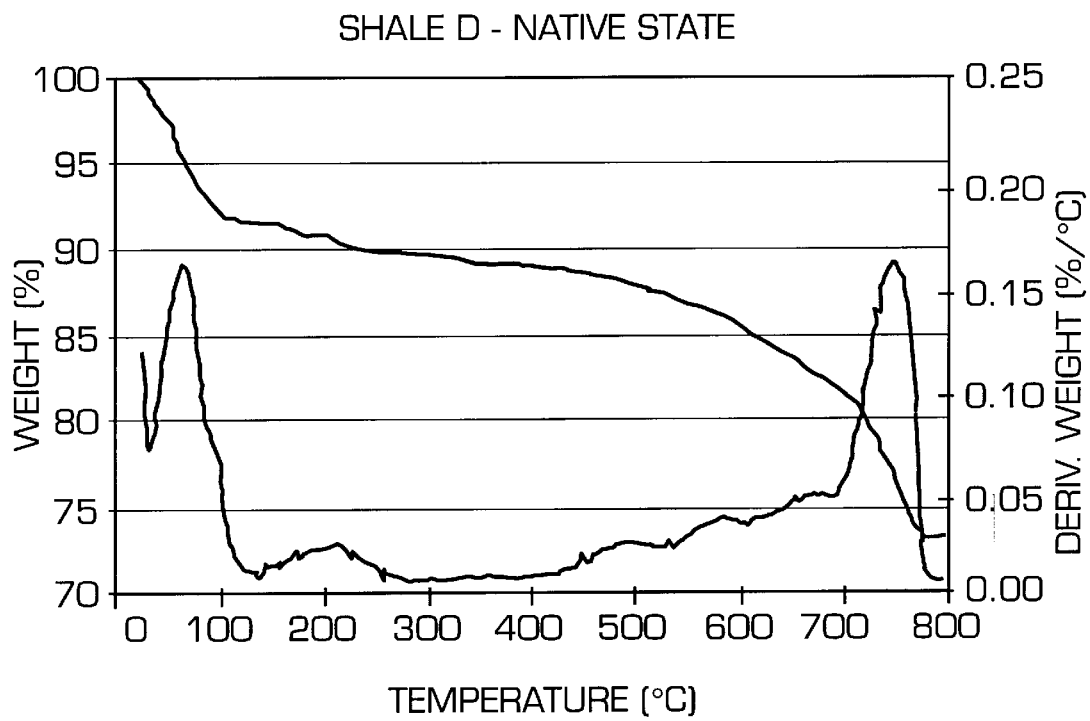
FIG. 12 attached is a TGA graph for another sample of Shale D in the native state.

FIGS. 11 and 12 illustrate TGA graphs of different samples of same Shale D in the native, downhole state. The close similarity of both graphs indicate that TGA may be used as a trustful analytical tool.

Interaction of Aqueous Salt Solutions with a Shaly Sample

Figure 13:
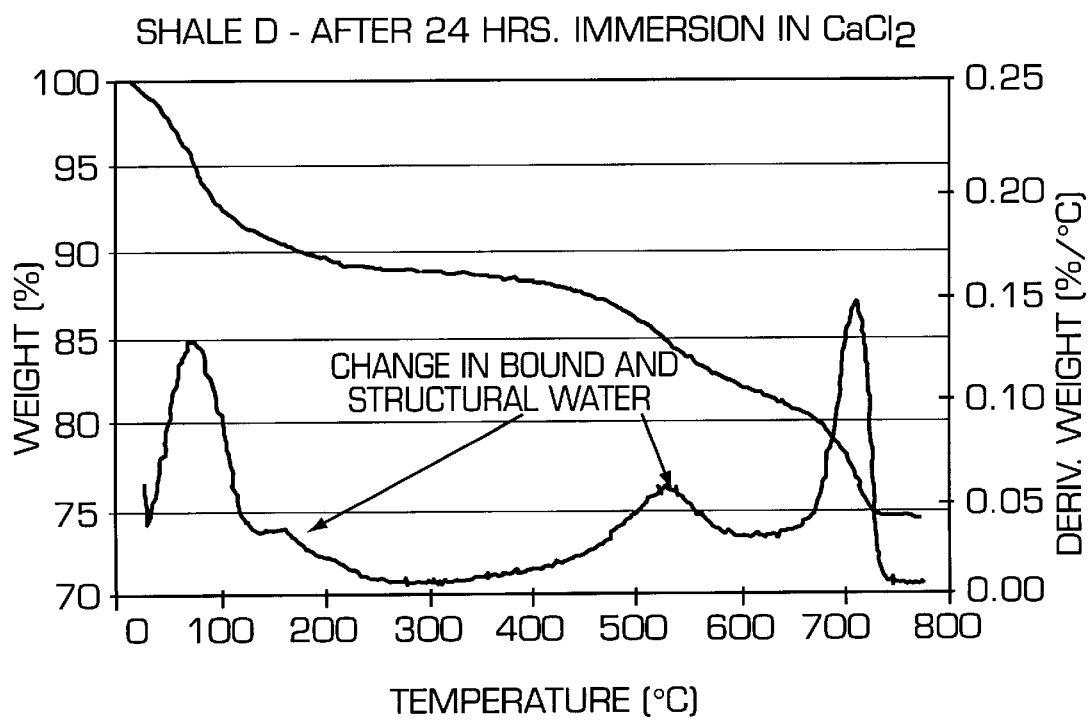
FIG. 13 attached is a TGA graph for a sample of Shale D after 24 hours immersion in $CaCl_2$ 35% w/w ($A_w$=0.50).
Figure 14:
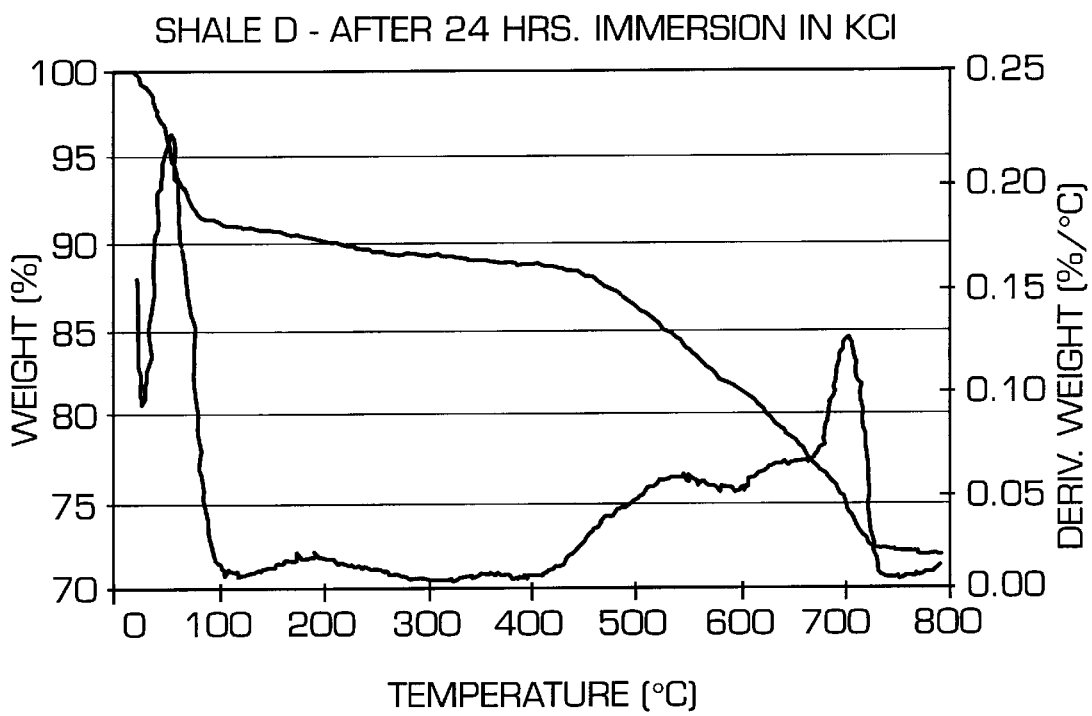
FIG. 14 attached is a TGA graph for a sample of Shale D after 24 hours immersion in KCl 25% w/w ($A_w$=0.85).
Figure 15:
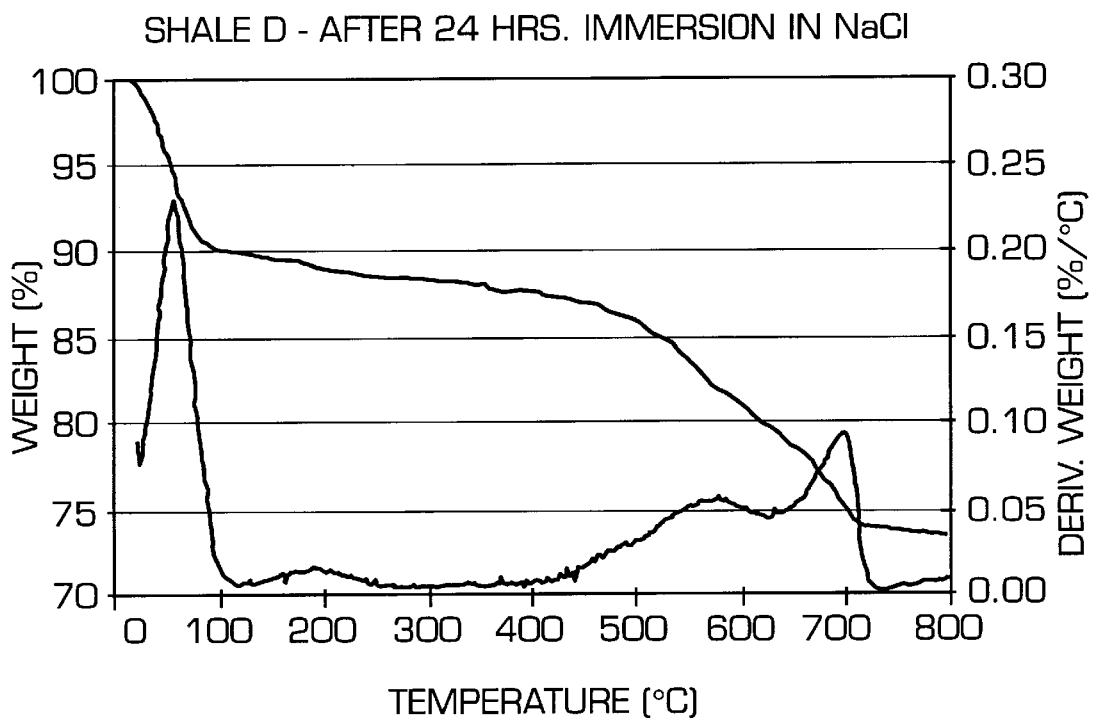
FIG. 15 attached is a TGA graph for a sample of Shale D after 24 hours immersion in NaCl 24% w/w (Aw=0.78).

FIGS. 13 to 15 are TGA graphs of the effect of salt solutions on shales.

For each salt solution, TGA tests were effected on the shale sample before immersion and after each 24 hours periods of immersion. Typically, the samples remained immersed in the solutions for 5 days, and were then immersed in de-ionized water until no further variation in structure could be observed. This aimed at determining the change in structure as a function of immersion period, and then checking the influence of the activity of the aqueous salt solution on the shaly sample. The most stringent situation is pictured when the sample is immersed in de-ionized water after a certain period of imersion in a salt solution.

Immersion in a $CaCl_2$ Aqueous Solution

FIG. 13 shows the modification in water distribution caused by immersion of a preserved shaly sample in a 35% aqueous $CaCl_2$ solution. The activity of this solution is $A_w=0.5$. A comparison of TGA graph of FIG. 13 and that of FIG. 11 of the downhole, native state of the same shale shows that bound and structural water have been altered by immersion in the salt solution. The inflection observed in the derivative curve below 100° C. has been eliminated due to the change in the interlayer water of the smectite. On the other hand, calcite content has not been significantly changed. As can be observed in FIG. 13, no significant change in water distribution could be observed after 24 hours immersion in the $CaCl_2$ solution. Although not illustrated, after 48 hours immersion in $CaCl_2$ solution the TGA graph did not show any modification.

Immersion in Alkaline Salts Aqueous Solution: KCl and NaCl

FIG. 14 shows the TGA graph for a sample of shale D after 24 hours immersion in an aqueous, 25 w/w% KCl solution of activity $A_w=0.85$ while FIG. 15 shows the TGA graph for a sample of shale D immersed in a 24% w/w NaCl aqueous solution ($A_w=0.78$). The effect of the immersion of a shale in alkaline salt solutions is similar, if the salt is KCl or NaCl. The final result is a flat derivative. Structural water is modified in similar way for both alkaline solutions, the observed modification being very different from that seen in the case of the $CaCl_2$ solution. Bound water changes quicker in the presence of NaCl and slower in the case of KCl and in both cases all the modifications occur during the first 24 hours. A reduction in calcite may be observed.

Upon contact with a NaCl solution the inflection related to smectite in the first portion of the derivative curve is eliminated.

Comments on the Interaction of a Shale and Aqueous Salt Solutions

The TGA graphs of FIGS. 13 to 15 show that immersion of a preserved shale in salt solutions produces a profound change in the shale, affecting even its structure. Not only free water is moving in or out of the shale, but cations and anions must be exchanging between the solution and the pore fluid in order to alter the shale structure. It is observed that each salt alters the structure in a different manner. The exchange of cations and anions is to be expected since the so-called semi-permeable membrane is assumed to be very weak when a shale is immersed in a water solution.

The change in calcite content resulting from the contact of the shale with different salt solutions is to be stressed since immersion in $CaCl_2$ did not significantly altered the content of this mineral in the sample, while immersion in NaCl and KCl did result in a reduction in calcite.

The reaction of calcite in water is given by the following equations (1) and (2):

$$CaCO_3(s) \leftrightarrow Ca^{2+}(aq) + CO_3^{2-}(aq) \quad (1)$$

$$CaCO_3 + H_2O \leftrightarrow Ca^{2+} + HCO_3^- + OH^- \quad (2)$$

When exposed to the quasi-saturated calcium solution there is no more calcium available for dissolution. However, immersion in sodium and potassium chloride aqueous solutions requires that some calcite be dissolved, so that chemical equilibrium can be reached.

The fact that most of the changes in the shale structure were observed in the first 24 hours of exposure of the sample to the solutions is an evidence against the accepted theory that instabilities in the field should be a consequence of shale-mud interaction. Time-delayed failures in shales cannot be explained using the argument that the fluid-shale interaction changes the rock, weakening it. No reduction in strength was observed by immersing the samples in the salt solutions, even though swelling was observed by adsorption of fluid and increase in weight. Only when the sample was contacted with de-ionized water did the rock lose some strength.

Immersion in De-ionized Water

Figure 16:
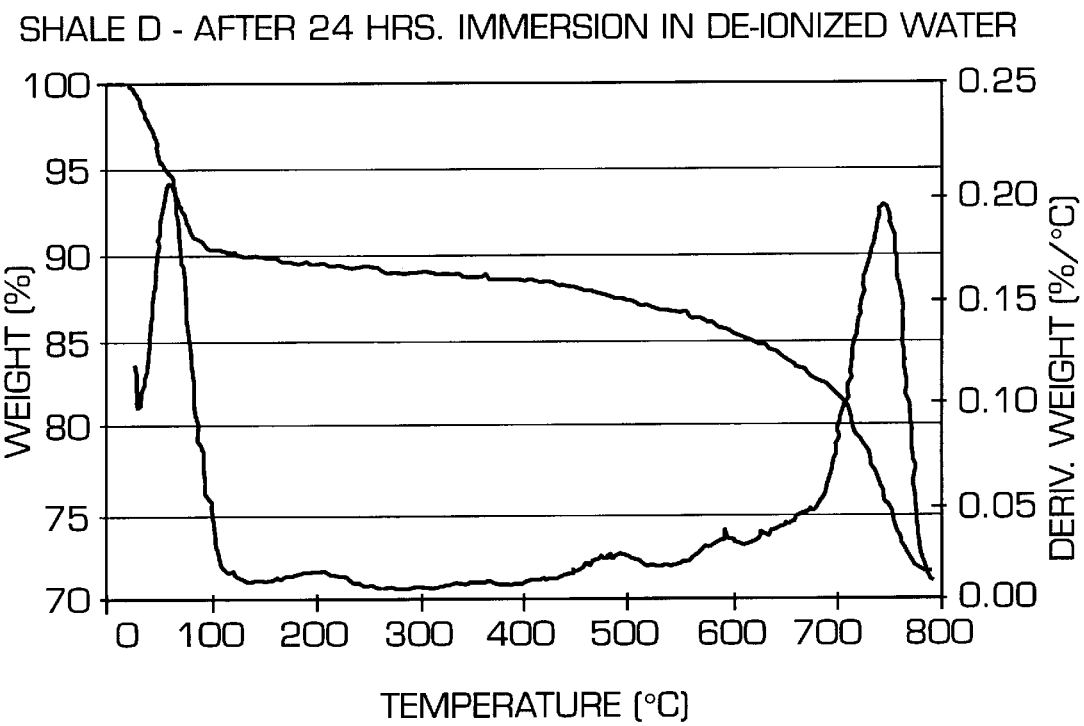
FIG. 16 is a TGA graph for a sample of shale D after 24 hours immersion in de-ionized water.

FIG. 16 illustrates a TGA graph for a sample of shale D after 24 hours immersion in de-ionized water. Activity $A_w$ is 1.00. Only the free and bound water were altered when shale Petr-D was immersed in de-ionized water. Structural water and calcite content remained the same throughout the duration of the test. Absorption of water is clear, with a direct consequence on the strength of the rock. Change in bound water took some time, reproducing the same behavior as that of the immersion in KCl. All other features of the shale remained constant.

Immersion in Absolute Ethanol

Figure 17:
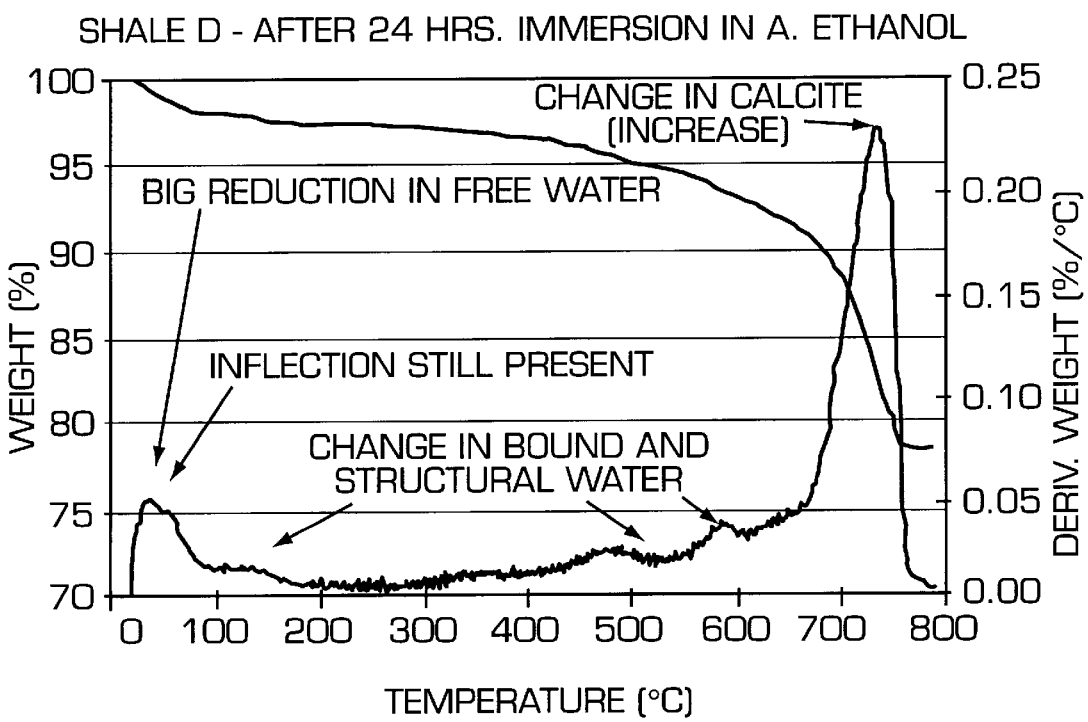
FIG. 17 is a TGA graph for a sample of shale D after 24 hours immersion in absolute ethanol.

FIG. 17 illustrates the observed changes undergone by shale D after immersion in an alcohol such as absolute ethanol. Shale dehydration is clear when immersed in an alcohol. A huge reduction in the first peak in the derivative curve shows that the free water reduced significantly relative to the original level. Bound water was also modified. An increase in calcite is evident. Even though a change in structural water did happen, this modification was not as strong as that observed as a result of the immersion of the shale in salt solutions. It is important to notice the presence of the inflection in the derivative curve after some dehydration has taken place. This indicates that the interlayer water of the smectite was not strongly affected, as in the case of the salt solutions mentioned previously.

Because of the dryness of the shale sample, immersion in de-ionized water produced a huge increase in free water content. However, all the other features remained the same except for a slight change in bound water. The adsorption of a great amount of water led the sample to completely lose its strength after only 24 hours or immersion in de-ionized water.

Immersion in CaCl$_2$OBM

In order to determine the interaction of a fluid actually employed in the field such as an oil-based-mud (OBM) and a shale, Shale D was immersed in an OBM where the water phase was CaCl$_2$ ($A_w$=0.39).

Figure 18:
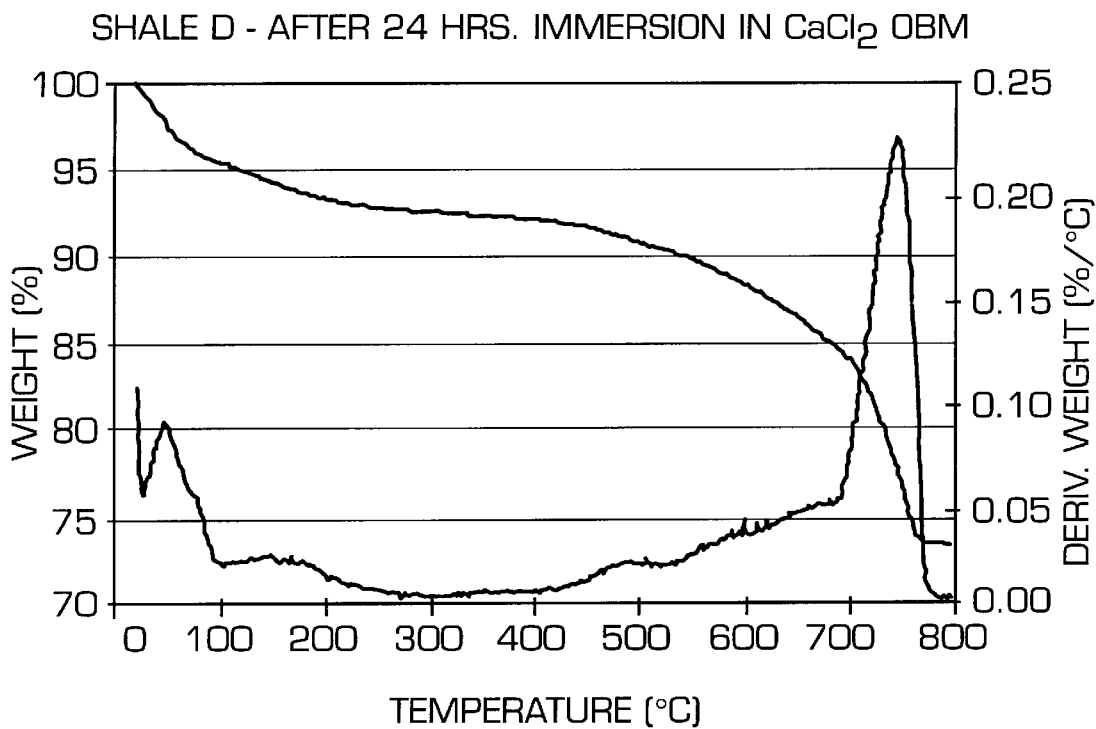
FIG. 18 is a TGA graph for a sample of shale D after 24 hours immersion in OBM with $CaCl_2$ ($A_w$=0.39) as water phase.

FIG. 18 shows that changes in calcite content and in structural water are not significant when a shale is immersed in an OBM where the water phase is calcium chloride. As in other cases, these changes occur predominantly in the first 24 hours of exposure. The interlayer water in the smectite is preserved, as may be noticed by the inflection in the derivative curve.

Immersion in KCl OBM

Figure 19:
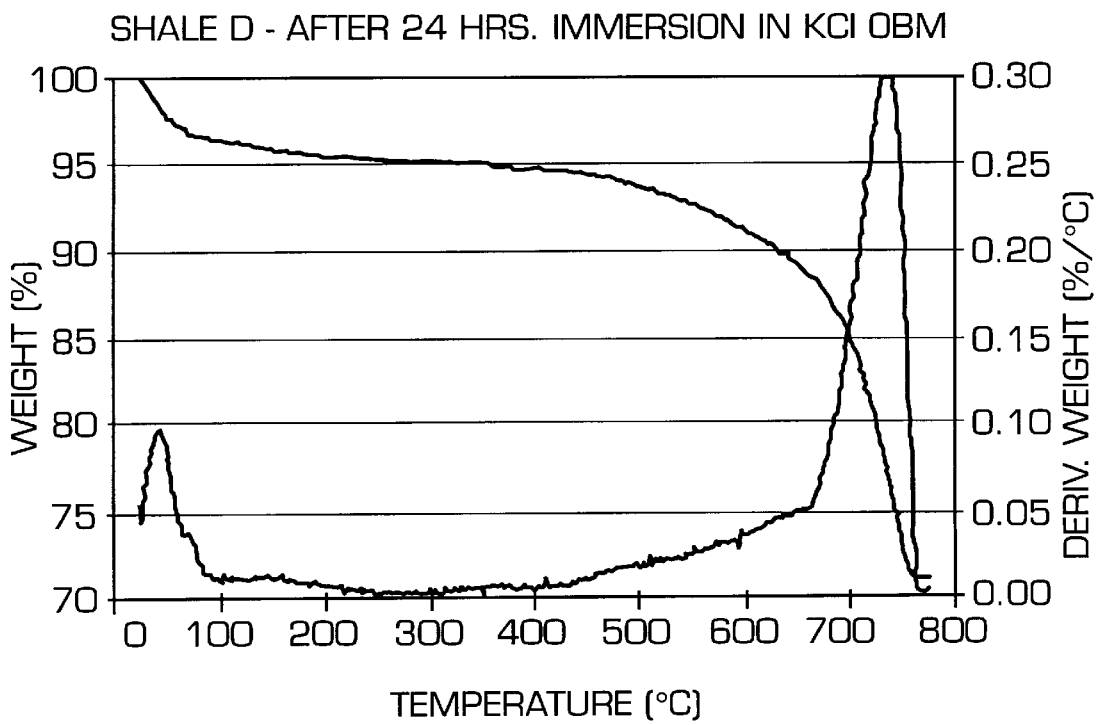
FIG. 19 is a TGA graph for a sample of shale D after 24 hours immersion in OBM with KCl ($A_w$=0.84) as water phase.

The activity of the water phase was $A_w$=0.84. FIG. 19 illustrates the interaction of shale D and OBM with KCl as water phase. A similar behavior to that observed in the case where the water phase is CaCl$_2$ is observed in the case of KCl as water phase. Reduction in free water preserves the inflection, and changes are mainly limited to bound water. Close observation of the graphs indicate that the change in bound water is slightly different from that observed with calcium chloride OBM, which suggests that the different cations might be playing an important role even when OBM is used.

Immersion in NaCl OBM

Figure 20:
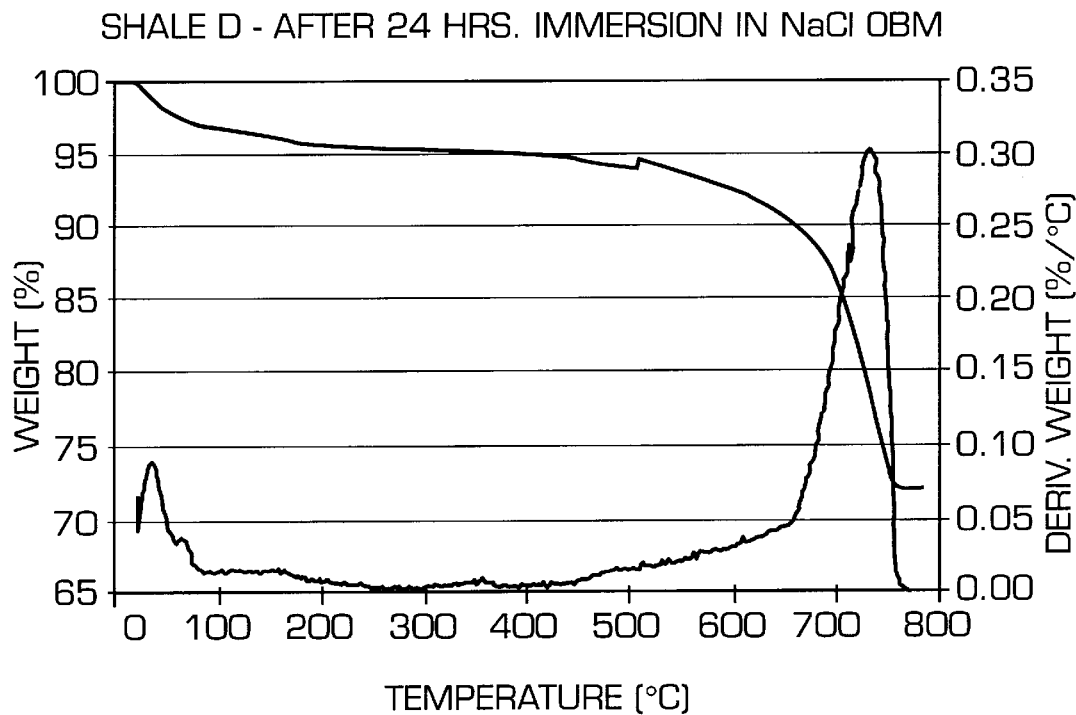
FIG. 20 is a TGA graph for a sample of shale D after 24 hours immersion in OBM with NaCl 24% w/w ($A_w$=0.75) as water phase.

The activity of the water phase was $A_w$=0.75. FIG. 20 illustrates the TGA graph for the interaction of shale D and NaCl 24 w/w% OBM. A similar behavior is observed when the water phase contains sodium chloride. Reduction in free water and change in bound water, similar to the KCl OBM. The inflection in the derivative curve is also present at all times.

Immersion in OBM with Fresh Water as Water Phase

Figure 21:
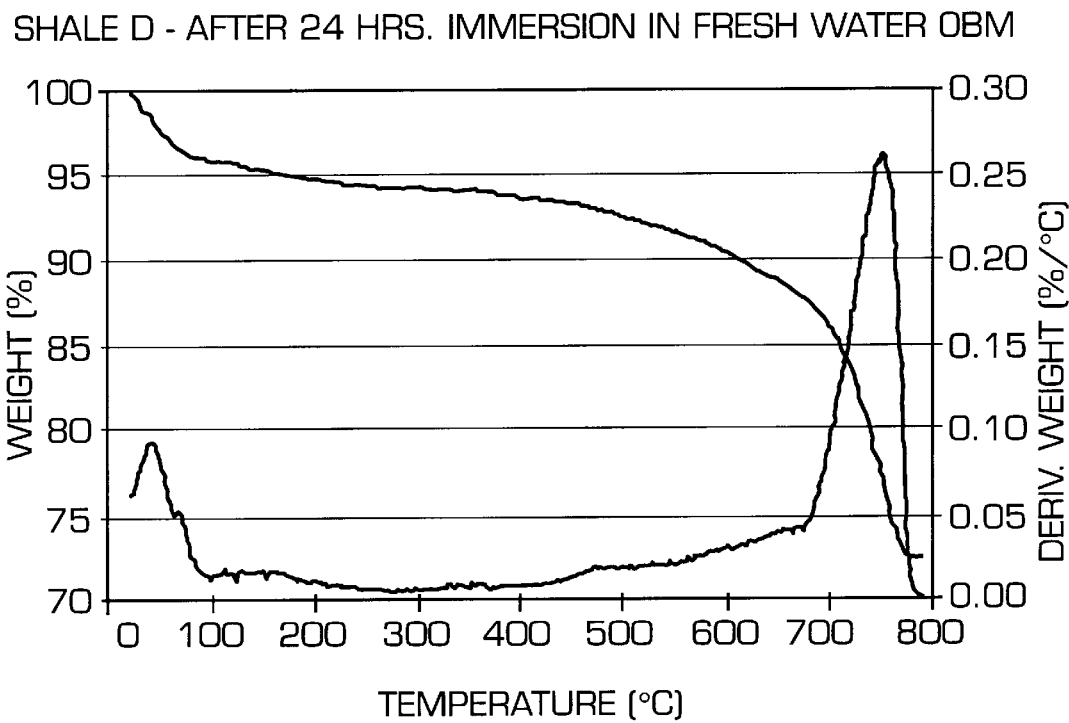
FIG. 21 is a TGA graph for a sample of shale D after 24 hours immersion in OBM with fresh water ($A_w$=0.99) as water phase.

FIG. 21 illustrates this situation. The activity of the water phase is $A_w$=0.99. The interaction of shale D with fresh water OBM shows the most surprising result. The observed change in the rock is almost the same as that observed when this shale is contacted with salted water. Reduction in free water with maintenance of the inflection in the derivative, unaltered calcite content and structural water, and a change in bound water, in a similar way as that observed for other OBMs.

When using the TGA technique, in addition to the mass curve, its derivative with respect to time or temperature is equally recorded during the experiment under way. By keeping a constant heating rate (typically 10° C./min) the derivative curve indicates different events with distinct peaks. Each peak characterizes a reaction with generation of a gas that is being removed. The importance of the derivative curve is that each mineral has a typical signature, with each peak occurring at a defined temperature. The derivative curve for a sample exhibits a signature that includes different events, since the rock is composed of several minerals, with varying proportions. By comparing the rock signature with the individual mineral curves, their presence may be identified.

COMPARATIVE EXAMPLES USING THE XRD TECHNIQUE

Although X-Ray Diffraction (XRD) is a widely-spread analytical tool in the oilfield technique, the results obtained by applying it do not include the characterization of the water associated with the different clay minerals. This is due to the fact that the sample to be submitted to a XRD analysis is prepared by drying and milling the shaly sample, thus eliminating all water from it. This is a fundamental limitation when shale-fluid interaction studies are under way, since it is well-known that water is present in clay minerals as free, interlayer, bound and crystalline water, and plays a decisive role in controlling the reactivity of a shale when it contacts a water solution. It is also of common knowledge that the amount and distribution of water in a shale actually controls the rock reactivity.

XRD is a semi-quantitative analytical tool used to characterize the composition of rocks which provides the relative amount of each mineral present. Based on the rock composition, decisions regarding the types of drilling and completion fluids are usually made.

However, the XRD technique, besides not being able to ascertain the water content of a shale and its change when in contact with different fluid solutions, may show unacceptable discrepancies when applied in different laboratories, this leading to serious consequences at the time of the choice of the drilling and completion fluid for a particular oil well.

Figure 22:
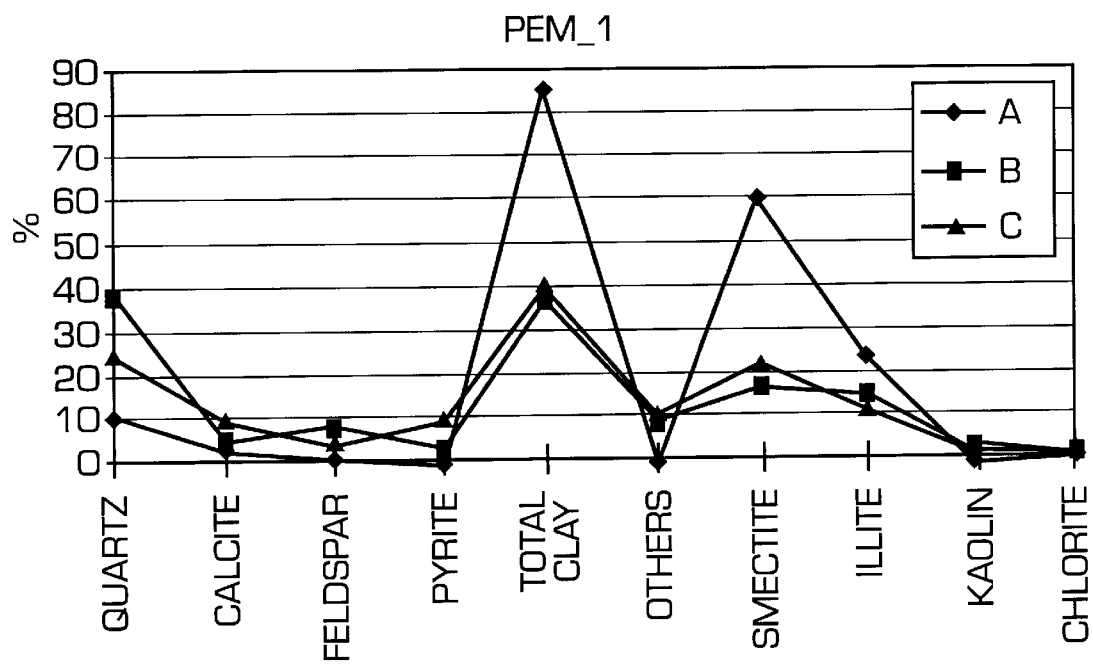
FIG. 22 is a XRD graph showing the mineralogy of a Pem-1 sample.
Figure 23:
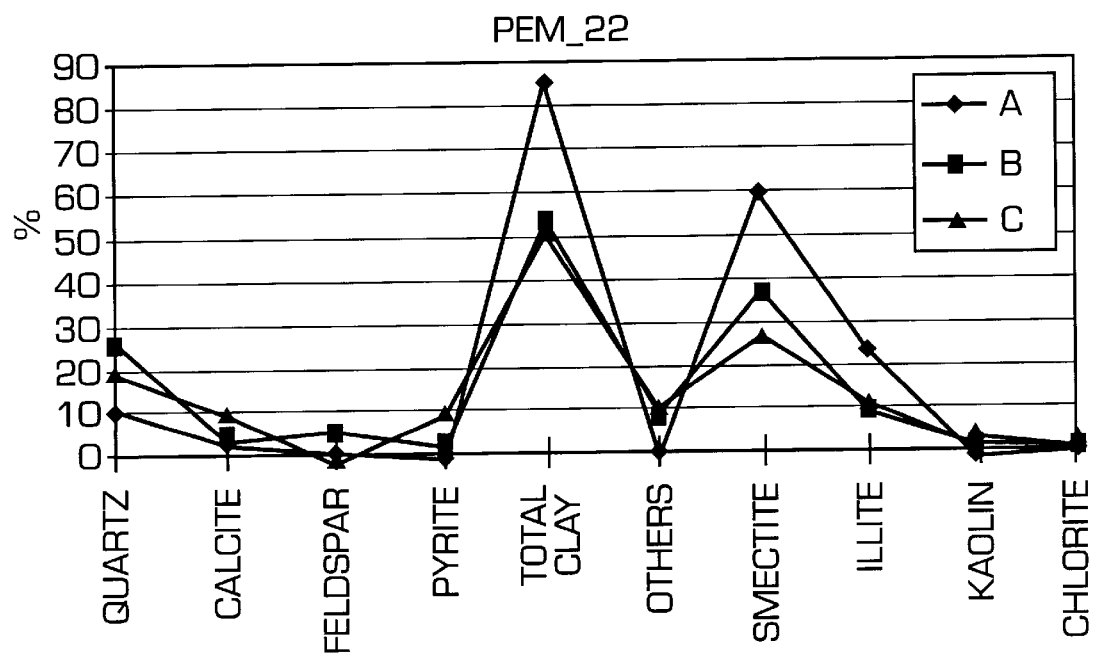
FIG. 23 is a XRD graph showing the mineralogy of a Pem-22 sample.

In order to check the reproducibility of the XRD method as compared to the TGA analytical tool as applied in the present application, the Applicant has tested adjacent pieces of core from different wells which were sent to three different laboratories, A, B and C. Results from two laboratories are in good agreement, but the third one shows discrepancies. FIG. 22 shows the XRD mineralogy of Pem-1 shale, where total clay is the sum of smectite+illite+ kaolinite+chlorite, while FIG. 23 shows the XRD mineralogy of Pem-22 shale, the total clay being the sum of same clays as in FIG. 22. Discrepancies among the results furnished by the various laboratories are visible as for the contents of smectite and illite, which are reflected in the total amount of clay. Laboratory A reported much higher values for total clay and smectite and illite content while laboratories B and C report closer results.

As FIGS. 7 and 8 report the TGA graphs of the same samples, a comparison is made possible between the two techniques.

The Table below presents the smectite contents in percent as determined from XRD (laboratories A, B and C).

TABLE

| Smectite Content in Sample (XRD) | Lab. A | Lab. B | Lab. C |
|---|---|---|---|
| Pem-1 | 60 | 18 | 21 |
| Pem-22 | 53 | 35 | 28 |

The results of the Table above show that Laboratory A indicates higher smectite content for Pem-1 than for Pem-22, while Laboratories B and C indicate the opposite. However, according to FIGS. 7 and 8 which illustrate the TGA graphs of the same samples, the smectite content of Pem-1 is actually much lower than the content of the same clay mineral in Pem-22. So, taking into account the figures provided by Laboratory A to direct the choice of a drilling fluid would lead the user to gross errors since the sample is actually a low smectite rock as indicated by the TGA graph.

Since shale reactivity is usually associated with clay and smectite content, depending on the laboratory in charge of the analysis, the conclusion would have been that the tested samples were very reactive, this implying in massive use of additives or even an oil-based mud (OBM), of high cost. On the contrary, another laboratory could have found lower clay contents, and consequently would have recommended a different drillling fluid. Therefore, the reliability of different laboratories is to be carefully checked when using XRD analysis as a tool to determine the composition of the most adequate drilling fluid to contact a high-clay shale.

The comparison of the results provided by TGA as a tool for characterizing the different types of water in a shale: free, interlayer, bound and crystalline and the state-of-the-art technique—XRD—shows that TGA is an adequate, qualitative methodology to identify minerals and water content in shales. The use of TGA as a tool allows the characterization of free, interlayer, bound and crystalline water in a shaly sample, which is tested in a truly preserved state which in turn allows to determine the interaction of such preserved sample with various fluids. Besides, it is a low-cost, quick procedure, which needs small, 10 to 80 mg samples, using an instrument which is of straightforward use by technical personnel.

Thus, TGA is a useful tool for detecting swelling of a clay-rich rock such as a shale through the changes in kind and content of water. Further, by immersing a clay-rich shale in a test fluid TGA analysis makes possible to determine the variation of the content of water in that sample. On the other hand, if that content is not altered by immersion in the test fluid, this means that the test fluid is neutral to the shale. As stated hereinbefore, these conclusions make the body of an entirely new approach to the problem of shale-fluid interaction.

Quantitative Determination of Minerals and Water Content of a Clay-rich Sample

As mentioned hereinbefore concerning FIG. 4, the present method is a useful tool not only for the qualitative, but also for the quantitative determination of a mineral in a shale, provided its peak is well characterized in the TGA graph and the chemical reaction undergone by the mineral is known. Thus, FIG. 4 illustrates a typical case where calcite is the well-characterized mineral in the TGA graph. Besides, the chemical reaction undergone by calcite on heating in the TGA instrument is well-known:

$$CaCO_3(s) \rightarrow CaO(s) + CO_2(g)/\text{*}$$

Calcite quantification may be inferred from the equation above, knowing the amount of gaseous $CO_2$ released. Since 1 mole of calcite yields 1 mole of $CO_2$, adding the atomic mass of each element leads to the weight in grams of each mole of the compounds:

1 mole of $CaCO_3 = 40 + 12 + 3 \times 16 = 100$ g 1 mole of $CO_2 = 12 + 2 \times 16 = 44$ g Therefore, 100 g of calcite yield 44 g of $CO_2$. From FIG. 4, the total amount of $CO_2$ is 5.06 g. The amount of calcite in that sample should be then equivalente to: Amount of calcite=$(100/44) \times$mass of $CO_2 = 2.27 \times 5.06$ mg=11.486 mg.

Since the calcite sample weights 11.48 mg, the percentage of calcite in that sample is 100% as espected.

A calcium carbonate laboratory sample was also tested in the TGA. The total weight of the sample was 12.27 mg, and the weight loss from $CO_2$ release was 5.138 mg. By using the same procedure described above, the amount of $CaCO_3$ in the sample was found to be 11.66 mg. Therefore the calcium carbonate tested was not 100%, but 95% pure.

It can be seen that when just one reaction (one peak) is present in the TGA chart, quantification of the mineral may be accurately done. A more difficult situation is encountered when several components are mixed, and the peaks of different reactions overlap each other. In order to quantify each element, the same procedure should be done. The chemical reaction should be known, and the peak in the TGA chart must be easily isolated.

For multiple peaks, the TGA chart for a particular rock is compared to the TGA charts of the individual minerals. An estimation of the relative amount of each mineral may be derived from the height of each peak. Quantification of what is being removed from the sample is straightforward (water or $CO_2$, for example) and is obtained straight from the weight curve.

When the TGA instrument is coupled to a chromatographic analyzer the characterization of the evolved gas is also possible and greatly facilitated.

As for the determination of the amount of water in a sample, FIGS. 9 and 10 illustrate this feature of the present method.

The derivative curve (or bottom curve in the TGA graph) of FIG. 9 clearly indicates the peak of release of free water (up to 110° C.) is much larger than the corresponding peak in FIG. 10. Values for weight of water are obtained straight from the weight curve (the upper curve in the TGA graph). thus, on FIG. 9 this value is nearly 9% while on FIG. 10 this value is 2.5% in weight.

Another advantageous feature of the present method which is not to be found in the state-of-the-art techniques is that besides the quantitative determination of water in a sample, the derivative provides further the type or kind of water present in the sample. Thus on FIG. 9 interlayer and free water may be observed while on FIG. 10 only interlayer water is shown.

I claim:

1. A method for the evaluation of drilling fluids as a test fluid to be contacted with a shale-type rock or clay-rich rocks with the aid of Thermo-Gravimetric Analysis (TGA) which comprises the following steps:

collecting downhole samples of the clay-rich rock to be analyzed keeping it free from dehydration so as to preserve the downhole hydration condition and obtain preserved as collected samples known to be free from the effects of exposure to said drilling fluids;

determining information regarding a qualitative and quantitative mineral composition and structure, type and amount of water in said downhole shale or clay-rich rock by submitting a piece of the preserved sample to a TGA analysis;

immersing a sample of the same piece of clay-rich rock in the test fluid whose effect on the sample is to be evaluated;

analyzing the sample immersed in the test fluid in terms of structure and composition with the aid of TGA at regular time intervals;

comparing structure and composition of the as-collected, preserved sample as obtained by TGA analysis with the structure and composition of the sample which has been immersed in the test fluid, also obtained by TGA, with the structural modification of the shale being ascertained through the mathematical derivative curve of mass with respect to temperature.

2. A method according to claim 1, wherein the sample for TGA analysis is taken from a preserved core.

3. A method according to claim 1, wherein the sample for TGA analysis is taken from preserved cuttings.

4. A method according to claim 1, wherein the sample for TGA analysis should be free from contact with drilling fluid or mud.

5. A method according to claim 1, wherein the quantitative determination of a mineral composition in a clay-rich rock is ascertained from its peak in the TGA graph and the chemical reaction governing the decomposition of that particular mineral.

6. A method according to claim 1, wherein the TGA graph of the as-collected, preserved sample shows the free, bound, interlayer and crystalline water of the sample while the TGA graph of the same sample after immersion in a test fluid during different periods of time shows the quantitative changes in free, bound, interlayer and crystalline water.

7. A method according to claim 1, wherein the test fluid in which the clay-rich rock is to be immersed is an aqueous fluid containing an inorganic salt.

8. A method according to claim 1, wherein the test fluid in which the clay-rich rock is to be contacted is de-ionized water.

9. A method according to claim 1, wherein the test fluid in which the clay-rich rock is to be immersed is an oil-based mud (OBM) containing an inorganic salt in the aqueous phase.

10. A method according to claim 1, wherein the test fluid in which the clay-rich rock is to be immersed is an oil-based mud (OBM) containing an de-ionized water in the aqueous phase.

11. A method of using Thermo-Gravimetric Analysis for evaluating drilling fluids to be tested for their interaction with clay-rich rocks, comprising immersing clay-rich rocks in drilling fluids according to the method of claim 1.

* * * * *